(12) United States Patent
Arasappan et al.

(10) Patent No.: US 6,838,475 B2
(45) Date of Patent: Jan. 4, 2005

(54) IMIDAZOLIDINONES AS NS3-SERINE PROTEASE INHIBITORS OF HEPATITIS C VIRUS

(75) Inventors: Ashok Arasappan, Bridgewater, NJ (US); Tejal Parekh, Mountain View, CA (US); F. George Njoroge, Warren, NJ (US); Viyyoor Moopil Girijavallabhan, Parsippany, NJ (US); Ashit K. Ganguly, Upper Montclair, NJ (US)

(73) Assignee: Schering Corporation, Kenilworth, NJ (US)

( * ) Notice: Subject to any disclaimer, the term of this patent is extended or adjusted under 35 U.S.C. 154(b) by 374 days.

(21) Appl. No.: 09/909,077

(22) Filed: Jul. 19, 2001

(65) Prior Publication Data

US 2002/0102235 A1 Aug. 1, 2002

Related U.S. Application Data

(60) Provisional application No. 60/220,110, filed on Jul. 21, 2000.

(51) Int. Cl.$^7$ ................................................ A01N 43/50
(52) U.S. Cl. ........................... 514/398; 514/18; 514/19; 514/396; 514/401; 548/335; 548/337; 530/331
(58) Field of Search ............................ 514/18, 19, 396, 514/398, 401; 530/331; 548/335, 337

(56) References Cited

U.S. PATENT DOCUMENTS 6,407,066 B1 * 6/2002 Dressen et al. ............... 514/19

FOREIGN PATENT DOCUMENTS

| WO | WO 98/17679 | 4/1998 |
| WO | WO 00/09543 | 2/2000 |

OTHER PUBLICATIONS

Shiba, Tetsuo Bulletin of the Chemical Society of Japan 41(11), 2748–53, 1968.*

Szirtes Journal of Medicinal Chemistry 29(9), 1654–8, 1986.*

* cited by examiner

*Primary Examiner*—Christopher S. F. Low
*Assistant Examiner*—David Lukton
(74) *Attorney, Agent, or Firm*—Palaiyur S. Kalyanaraman

(57) ABSTRACT

The present invention discloses novel imidazolidinones which have HCV protease inhibitory activity as well as methods for preparing such compounds. In another embodiment, the invention discloses pharmaceutical compositions comprising such imidazolidinones as well as methods of using them to treat disorders associated with the HCV protease.

43 Claims, No Drawings

SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: junction sequence
<220> FEATURE:

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: Ala or Pro
<220> FEATURE:
<221> NAME/KEY: MISC_FEATURE
<222> LOCATION: (8)..(8)
<223> OTHER INFORMATION: Norvaline

<400> SEQUENCE: 1

Asp Thr Glu Asp Val Val Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-Gla
<220> FEATURE:
<221> NAME/KEY: MISC_FEATURE
<222> LOCATION: (5)..(5)
<223> OTHER INFORMATION: Cha

<400> SEQUENCE: 2

Asp Xaa Leu Ile Xaa Cys
1               5

<210> SEQ ID NO 3
<211> LENGTH: 8
<212> TYPE: PRT
<213> ORGANISM: Artificial Sequence
<220> FEATURE:
<223> OTHER INFORMATION: inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: Norvaline

<400> SEQUENCE: 3

Asp Thr Glu Asp Val Val Ala Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: Norvaline
```

<400> SEQUENCE: 4

Asp Thr Glu Asp Val Val Pro Xaa
1               5

IMIDAZOLIDINONES AS NS3-SERINE PROTEASE INHIBITORS OF HEPATITIS C VIRUS

This application claims priority from provisional application, Serial No. 60/220,110, filed Jul. 21, 2000.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel peptide compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3 . Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) Proc. Natl. Acad. Sci (USA) 91:888–892, Failla et al. (1996) Folding & Design 1:35–42. The NS3/NS4a cleavage site is also more tolerant of mutagenesis than the other sites. See, e.g., Kollykhalov et al. (1994) J. Virol. 68:7525–7533. It has also been found that acidic residues in the region upstream of the cleavage site are required for efficient cleavage. See, e.g., Komoda et al. (1994) J. Virol. 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) Biochem. 36:9340–9348, Ingallinella et al. (1998) Biochem. 37:8906–8914, Llinas-Brunet et al. (1998) Bioorg. Med. Chem. Lett. 8:1713–1718), inhibitors based on the 70-amino acid polypeptide eglin c (Martin et al. (1998) Biochem. 37:11459–11468, inhibitors affinity selected from human pancreatic secretory trypsin inhibitor (hPSTI-C3) and minibody repertoires (MBip) (Dimasi et al. (1997) J. Virol. 71:7461–7469), $CV_HE2$ (a "camelized" variable domain antibody fragment) (Martin et al.(1997) Protein Eng. 10:607–614), and α1-antichymotrypsin (ACT) (Elzouki et al.) (1997) J. Hepat. 27:42–28). A ribozyme designed to selectively destroy hepatitis C virus RNA has recently been disclosed (see, BioWorld Today 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Reference is made to A. Marchetti et al, Synlett, S1, 1000–1002 (1999) describing the synthesis of bicylic analogs of an inhibitor of HCV NS3 protease. A compound disclosed therein has the formula:

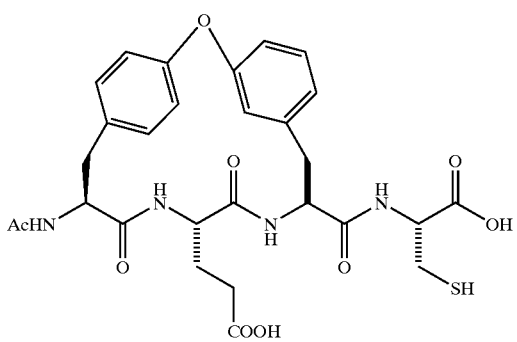

Reference is also made to W. Han et al, Bioorganic & Medicinal Chem. Lett, (2000) 10, 711–713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

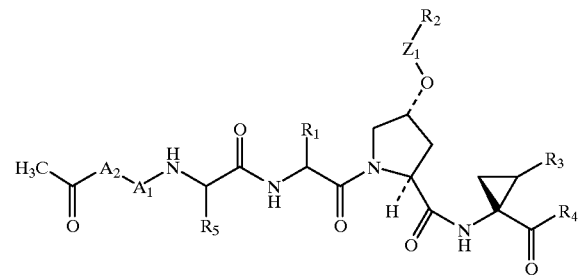

where the various elements are defined therein. An illustrative compound of that series is:

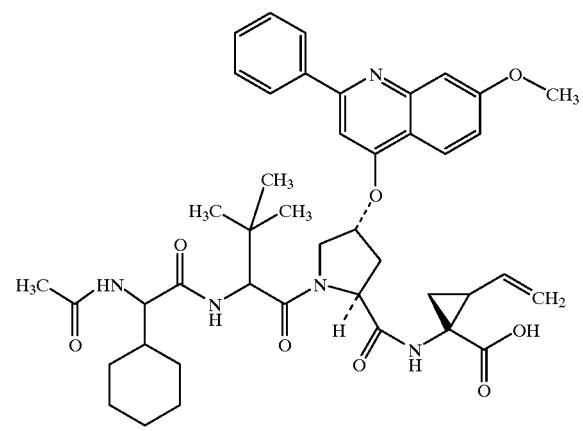

Reference is also made to WO 00/09543 (Assignee: Boehringer Ingelheim Limited; Published Feb. 24, 2000) which discloses peptide derivatives of the formula:

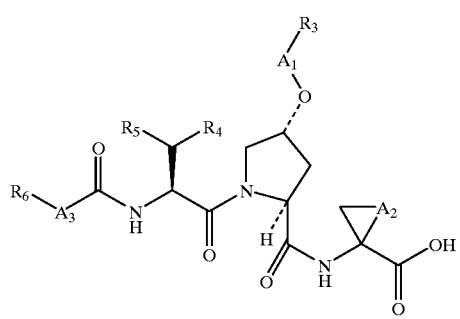

where the various elements are defined therein. An illustrative compound of that series is:

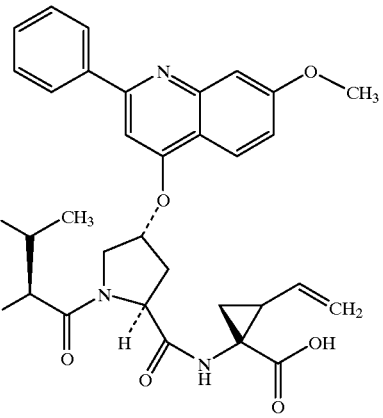

Current therapies for hepatitis C include interferon-α (INF$_\alpha$) and combination therapy with ribavirin and interferon. See, e.g., Beremguer et al. (1998) *Proc. Assoc. Am. Physicians* 110 (2):98–112. These therapies suffer from a low sustained response rate and frequent side effects. See, e.g. Hoofnagle et al. (1997) *N. Engl. J. Med.* 336:347. Currently, no vaccine is available for HCV infection.

Pending and copending U.S. patent applications, Ser. No. 60/220,109, filed Jul. 21, 2000, Ser. No. 60/220,107, filed Jul. 21, 2000, Ser. No. 60/220,108, filed Jul. 21, 2000, Ser. No. 60/220,101, filed Jul. 21, 2000, Ser. No. 60/254,869, filed Dec. 12, 2000, Ser. No. 60/194,607, filed Apr. 5, 2000, and Ser. No. 60/198,204, filed Apr. 19, 2000 disclose various types of peptides as NS-3 serine protease inhibitors of hepatitis C virus.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF INVENTION

In its several embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The presently disclosed compounds generally contain about two or more amino acid residues and less than about twelve amino acid residues.

In its principal embodiment, the present invention provides an imidazolidinone of Formula I:

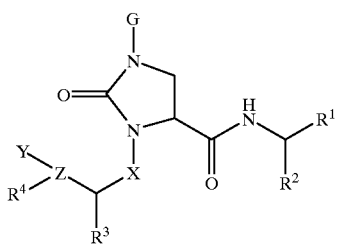

Formula I wherein:
  $R^1$ is $COR^5$ or $B(OR)_2$, wherein $R^5$ is selected from the group consisting of: H, OH, $OR^8$, $NR^9R^{10}$, $CF_3$, $C_2F_5$, $C_3F_7$, $CF_2R^6$, $R^6$, and $COR^7$ with $R^7$ being H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COO\ R^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COO\ R^{11}$, $CH(R^{1'})CONHCH(R^{2'})CONHCH(R^{3'})CONR^{12}R^{13}$, wherein $R^{1'}$, $R^{2'}$, $R^{3'}$, $R'$, $R^{11}$, $R^{12}$, and $R^{13}$ are independently selected from a group consisting of H, alkyl, aryl, heteroalkyl, heteroaryl, cycloalkyl, alkyl-aryl, alkyl-heteroaryl, aryl-alkyl and heteroaralkyl;
  Z is O, N, or CH;
  X is selected from the group consisting of: C=O, C=S and $(CRR')_p$;
  p is a number from 1–6;
  G is selected from the group consisting of: H, alkyl, aryl, heteroalkyl, heteroaryl, alkyl-aryl and alkyl-heteroaryl with the proviso that G may be additionally optionally and chemically-suitably substituted with $U^{11}$ or $U^{12}$;
  R, $R^2$, and $R^3$ may be the same or different and are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, ester, carboxylic acid, carbamate, urea, ketone, aldehyde, cyano, nitro; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;
  $R^4$ maybe present or absent, and if $R^4$ is present, $R^4$ is selected from H, alkyl, aryl; and
  Y is selected from the group consisting of H, alkyl, aryl, heteroalkyl, heteroaryl, cycloalkyl, arylalkyl, heteroarylalkyl, and U, where U is selected from alkylaryl, aryl-heteroaryl, alkyl-heteroaryl, alkylcarbonyl, arylalkylcarbonyl, arylcarbonyl, heteroalkylcarbonyl, heteroarylcarbonyl, cycloalkylcarbonyl, alkyloxycarbonyl, alkyl-aryloxycarbonyl, aryloxycarbonyl, arylalkyloxycarbonyl, heteroaryloxycarbonyl, heterocycloalkyloxycarbonyl, cycloalkyloxycarbonyl, alkylaminocarbonyl, arylaminocarbonyl, alkyl-arylaminocarbonyl, arylaminocarbonyl, arylalkylaminocarbonyl, heteroarylaminocarbonyl, cycloalkylaminocarbonyl, heterocycloalkylaminocarbonyl, alkylsulfonyl, arylsulfonyl, alkyl-arylsulfonyl, arylalkylsulfonyl, heteroarylsulfonyl, cycloalkylsulfonyl, and heterocycloalkylsulfonyl with the proviso that U may be additionally optionally and chemically-suitably substituted with $U^{11}$ or $U^{12}$; where
  $U^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl moiety, with the proviso that $U^{11}$ may be additionally optionally substituted with $U^{12}$; and
  $U^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from $U^{12}$. Furthermore, it is to be generally understood that the alkyl, heteroalkyl, alkenyl, heteroalkenyl, aryl, heteroaryl, cycloalkyl and heterocycloalkyl moieties may be optionally substituted, with the term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, and hydroxamate.

Additionally, the moiety:

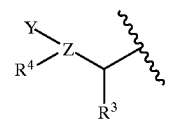

in Formula I may represent an arylalkyloxy group such as, for example, benzyloxy.

Some illustrative preferred examples for $R^2$ include the following:

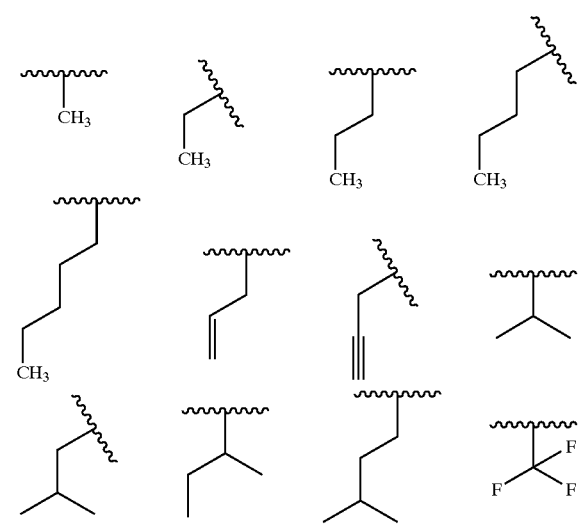

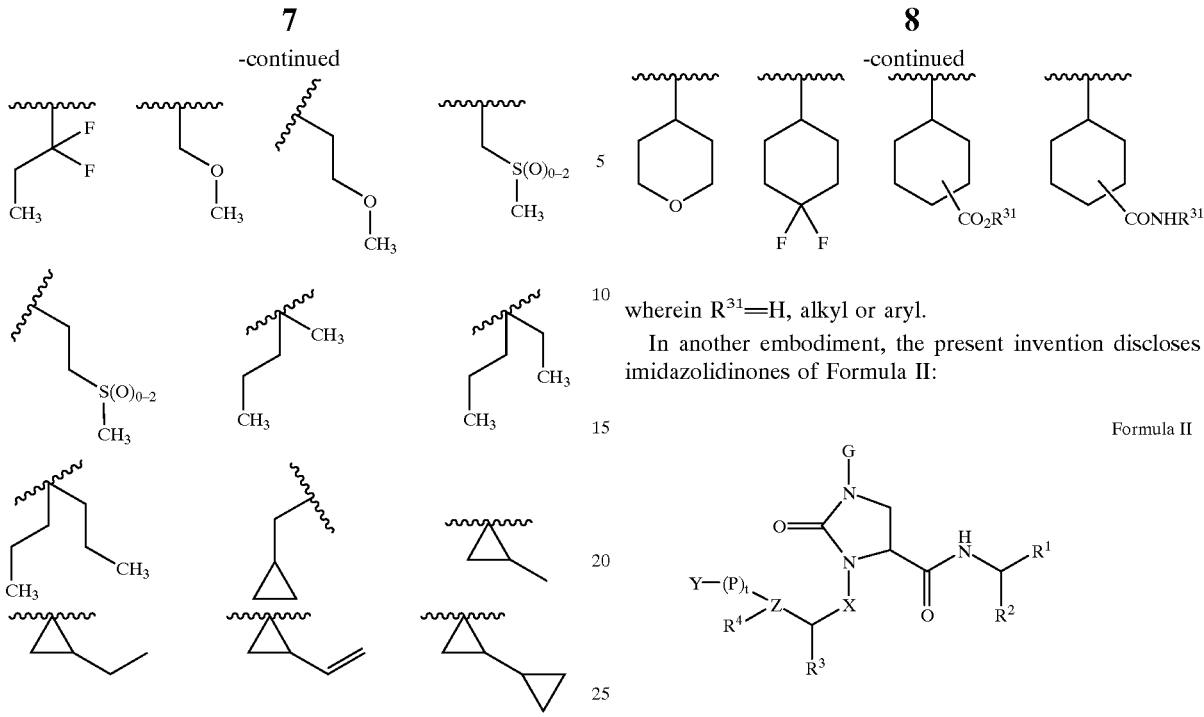

wherein $R^{31}$=H, alkyl or aryl.

In another embodiment, the present invention discloses imidazolidinones of Formula II:

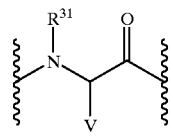

Formula II wherein $R^1$, $R^2$, $R^3$, $R^4$, G, X, Y and Z are as defined above, t is a number from 1 to 3, and the P moiety or moieties (when t is 2 or 3) may be the same or different, are amino acid residues represented by:

wherein V is selected from the group consisting of the following:

Some illustrative preferred examples for G include the following:

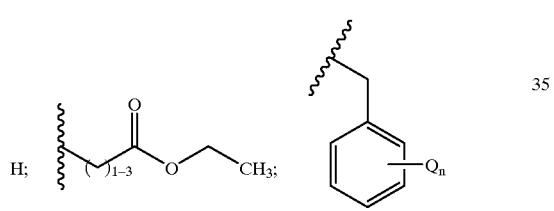

Some illustrative preferred examples for $R^3$ include the following:

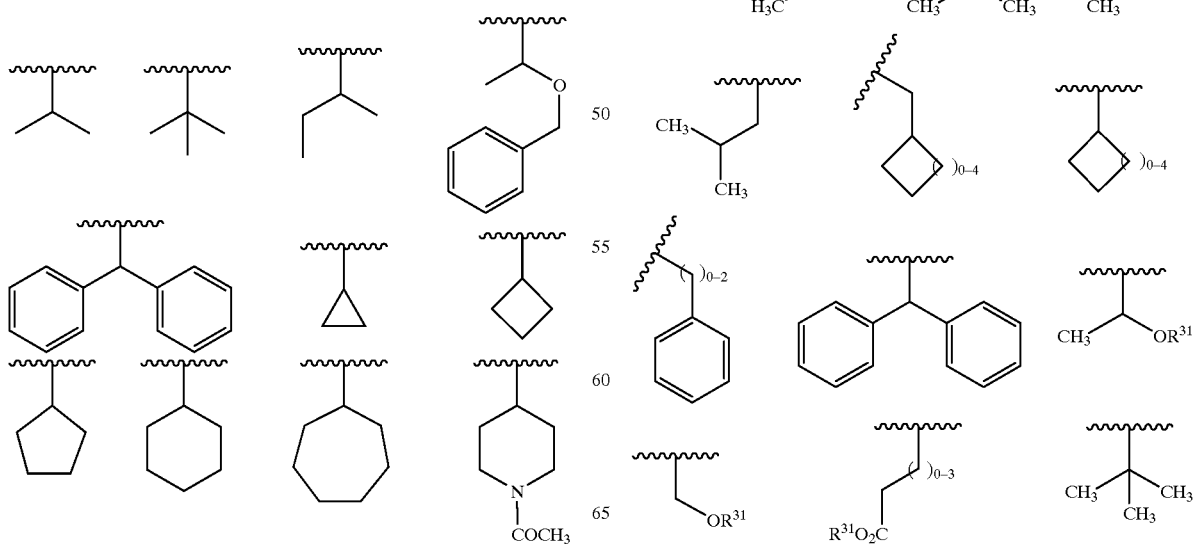

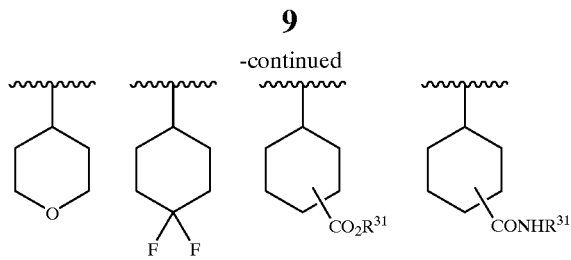

wherein $R^{31}$ is H, alkyl or aryl.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

- aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;
- aralkyl—represents a moiety containing an aryl group linked vial a lower alkyl;
- alkylaryl—represents a moiety containing a lower alkyl linked via an aryl group;
- cycloalkyl—represents a saturated carbocyclic ring having from 3 to 8 carbon atoms, preferably 5 or 6, optionally substituted.
- heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 3 to 9-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;
- halogen—represents fluorine, chlorine, bromine and iodine;
- heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; Such heteroaryl groups may also be optionally substituted.

Also included in the invention are tautomers, enantiomers and other optical isomers of compounds of Formula I and Formula II, as well as pharmaceutically acceptable salts and solvates thereof.

A further feature of the invention is pharmaceutical compositions containing as active ingredient a compound of Formula I or Formula II (or its salt, solvate or isomers) together with a pharmaceutically acceptable carrier or excipient.

The invention also provides methods for preparing compounds of Formula I and Formula II, as well as methods for treating diseases such as, for example, HCV and related disorders. The methods for treating comprise administering to a patient suffering from said disease or diseases a therapeutically effective amount of a compound of Formula I or Formula II, or pharmaceutical compositions comprising a compound of Formula I or Formula II.

Also disclosed is the use of a compound of Formula I and Formula II for the manufacture of a medicament for treating HCV and related disorders.

DETAILED DESCRIPTION OF PREFERRED EMBODIMENTS

In one embodiment, the present invention discloses compounds of Formula I and Formula II as inhibitors of HCV protease, especially the HCV NS3/NS4a serine protease, or a pharmaceutically acceptable derivative thereof, where the various definitions are given above.

Representative compounds of the invention which exhibit excellent HCV protease inhibitory activity are listed below along with their activity (ranges of $K_i^*$ values in nanomolar, nM). The Example numbers refer to the numbers for the various structures in the EXAMPLES section found in the later parts of this application.

TABLE 1

| HCV protease continuous assay results | |
|---|---|
| Example Number | $K_i^*$ (nM) |
| 1 | c |
| 2 | c |
| 3 | c |
| 4 | b |
| 5 | b |
| 6 | c |
| 7 | c |
| 8 | c |
| 9 | c |
| 10 | c |
| 11 | c |
| 12 | b |
| 13 | c |
| 14 | c |
| 15 | c |
| 16 | c |
| 17 | c |
| 18 | a |
| 19 | c |
| 20 | c |
| 21 | c |
| 22 | c |
| 23 | a |
| 24 | c |
| 25 | c |
| 26 | c |
| 27 | c |
| 28 | a |
| 29 | c |
| 30 | b |
| 31 | c |
| 32 | c |
| 33 | b |
| 34 | b |
| 35 | c |
| 36 | b |
| 37 | c |
| 38 | c |
| 39 | c |
| 40 | c |
| 41 | c |
| 42 | c |
| 43 | c |
| 44 | c |
| 45 | c |
| 46 | c |
| 47 | c |

TABLE 1-continued

HCV protease continuous assay results

| Example Number | Ki* (nM) |
|---|---|
| 48 | b |
| 49 | a |
| 50 | b |
| 51 | a |
| 52 | a |
| 53 | a |
| 54 | a |
| 55 | a |
| 56 | a |
| 57 | a |

HCV continuous assay Ki* range:
a = 1–1000 nM; b = 1001 nM–50000 nM; and c >50001 nM.

Some of the types of the inventive compounds and methods of synthesizing the various types of the inventive compounds of Formula I and Formula II are listed below, then schematically described, followed by the illustrative Examples.

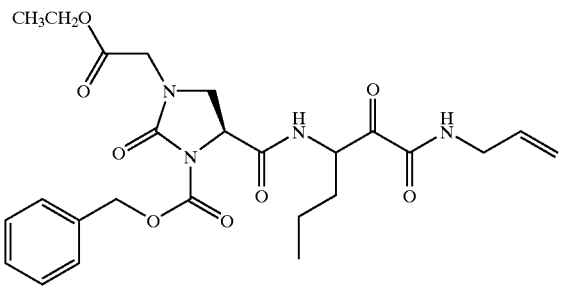

1

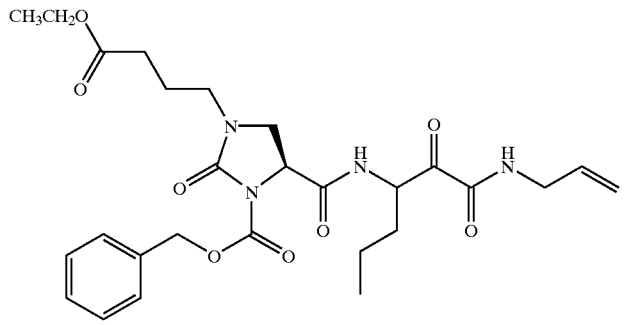

2

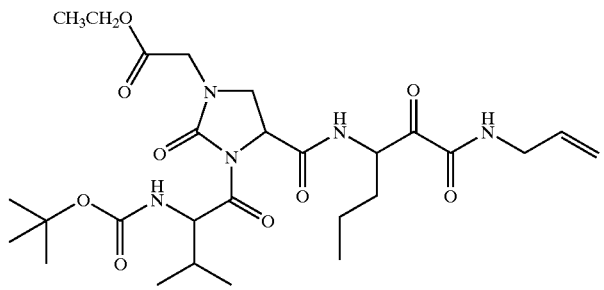

3

-continued
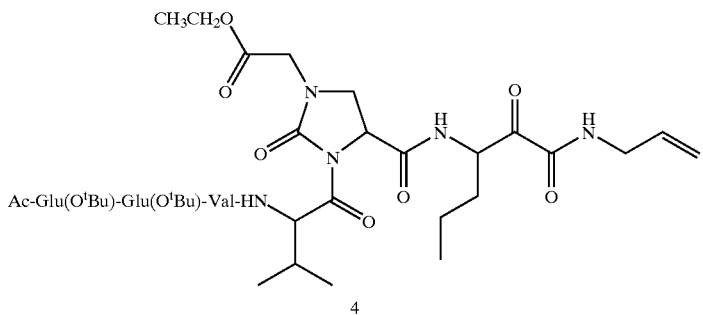
4
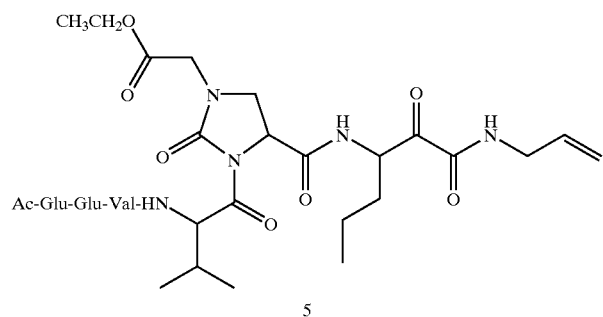
5
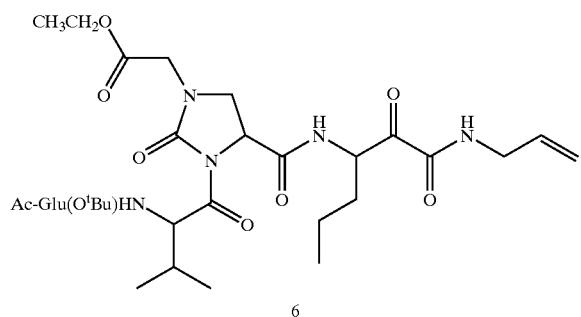
6
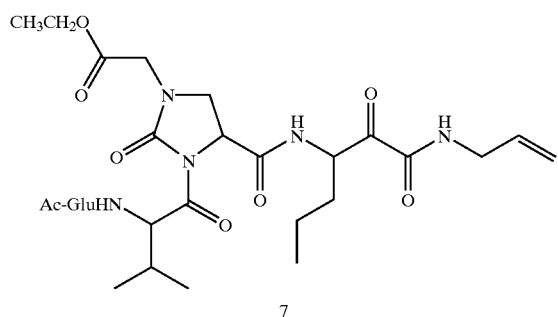
7
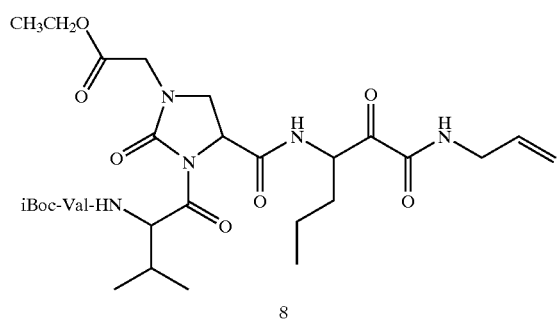
8

-continued
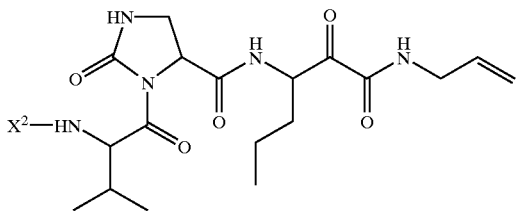
| Compound | X² |
|---|---|
| 9 | Boc-Val- (isomer 1) |
| 10 | Boc-Val- (isomer 2) |
| 11 | Ac-Glu(O$^t$Bu)-Glu(O$^t$Bu)-Val- |
| 12 | Ac-Glu-Glu-Val- |
| 13 | Boc |
| 14 | H |
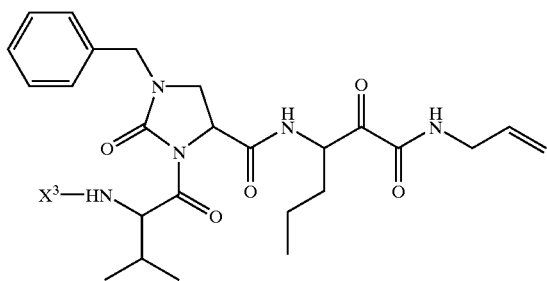
| Compound | X³ |
|---|---|
| 15 | Boc-Val- |
| 16 | Val- |
| 17 | Ac-Glu(O$^t$Bu)-Glu(O$^t$Bu)-Val- |
| 18 | Ac-Glu-Glu-Val- |
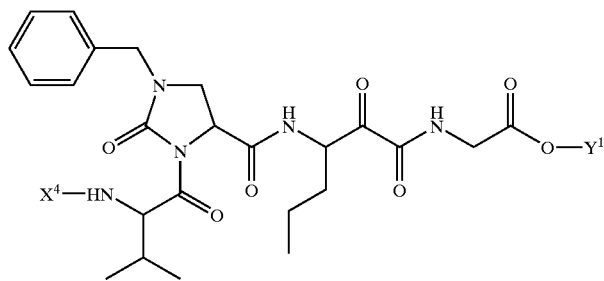
| Compound | X⁴ | Y¹ |
|---|---|---|
| 19 | Boc- | allyl |
| 20 | H | allyl |
| 21 | Boc-Val- | allyl |
| 22 | Ac-Glu(O$^t$Bu)-Glu(O$^t$Bu)-Val- | allyl |
| 23 | Ac-Glu-Glu-Val- | allyl |
| 24 | Boc-Val- | H |
| 25 | Ac-Glu(O$^t$Bu)-Glu(O$^t$Bu)-Val- | H |

-continued

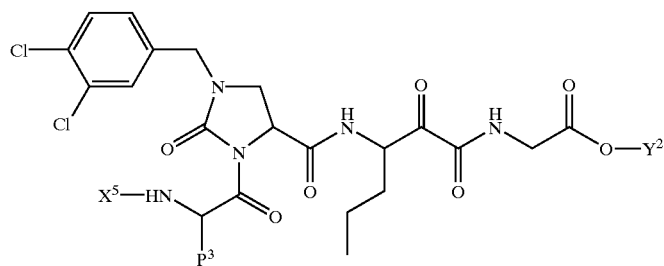

| Compound | X⁵ | Y² | P₃ |
|---|---|---|---|
| 26 | Boc-Val- | allyl | iPr |
| 27 | Ac-Glu(OᵗBu)-Glu(OᵗBu)-Val- | allyl | iPr |
| 28 | Ac-Glu-Glu-Val- | allyl | iPr |
| 29 | Boc- | benzyl | Chx |

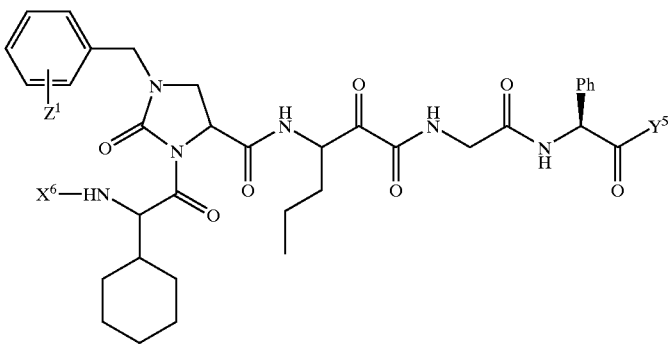

| Compound | X⁶ | Z¹ | Y⁵ |
|---|---|---|---|
| 30 | Boc- | 3,4-dichloro | —NH₂ |
| 31 | Boc- | 4-Bromo | —OBn |
| 32 | Boc- | 3-Bromo | —OBn |
| 33 | Boc- | 4-Chloro | —OBn |
| 34 | Boc- | 3-Chloro | —OBn |
| 35 | iBoc- | 3,4-dichloro | —NH₂ |
| 36 | iBoc- | 4-Bromo | —OBn |
| 37 | iBoc- | 3-Bromo | —OBn |
| 38 | iBoc- | 4-Chloro | —OBn |
| 39 | iBoc- | 3-Chloro | —OBn |
| 40 | Boc- | 4-Bromo | —OH |
| 41 | Boc- | 3-Bromo | —OH |
| 42 | Boc- | 4-Chloro | —OH |
| 43 | Boc- | 3-Chloro | —OH |
| 44 | iBoc- | 4-Bromo | —OH |
| 45 | iBoc- | 3-Bromo | —OH |
| 46 | iBoc- | 4-Chloro | —OH |
| 47 | iBoc- | 3-Chloro | —OH |

-continued

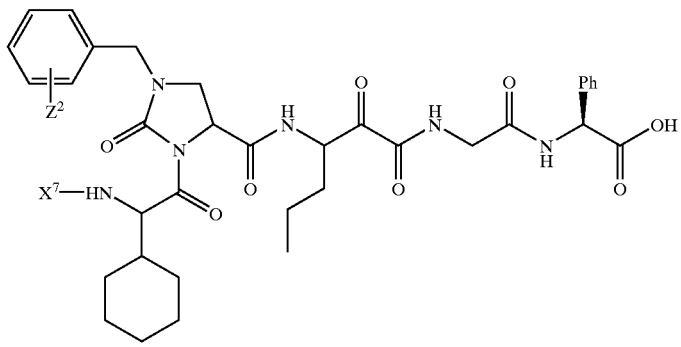

| Compound | X⁷ | Z² |
|---|---|---|
| 48 | iBoc- | H |
| 49 | Ac-Val- | H |
| 50 | iBoc- | 3,4-dimethyl |
| 51 | Ac-Val- | 3,4-dimethyl |
| 52 | iBoc- | 3-methyl |
| 53 | Ac-Val- | 3-methyl |
| 54 | Ac-Val- | 4-methyl |
| 55 | Ac-Val- | 3-methoxy |
| 56 | Ac-Val- | 4-methoxy |
| 57 | Ac-Val- | 4-$^t$-butyl |

Depending upon their structure, the compounds of the invention may form pharmacuetically acceptable salts with organic or inorganic acids, or organic or inorganic bases. Examples of suitable acids for such salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, $NH_4OH$, tetraalkylammonium hydroxide, and the like.

In another embodiment, this invention provides pharmaceutical composition comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy mode such as, for example, in combination with antiviral agents such as, for example, ribavirin and/or interferon such as, for example, α-interferon and the like.

As stated earlier, the invention includes tautomers, rotamers, enantiomers and other stereoisomers of the compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
MeOH: Methanol
EtOH: Ethanol
iPrOH: isopropanol
tBuOH: tert-Butanol
Et$_2$O: Diethyl ether
DME: Ethyleneglycol dimethylether
Boc: tert-Butyloxycarbonyl
iBoc: isobutyloxycarbonyl
Cbz: Benzyloxycarbonyl
Fmoc: 9-Fluorenylmethoxycarbonyl
DMSO: Dimethyl sulfoxide
TFA: Trifluoroacetic acid
HOBt: Hydroxybezotriazole
Hünigs base: Diisopropylethyl amine (DIPEA)
BOP: Benzotrizaol-1-yloxytris(dimethylamino) phosphonium hexafluorophosphate
HATU: O-(7-Azabenzatriazol-1-yl)-N,N,N',N',-tetramethyluronium hexafluorophosphate
TsOH: p-Toluenesulfonic acid
DMAP: 4-Dimethyl aminopyridine
DCC: Dicyclohexylcarbodiimide
MeCN: acetonitrile
Me: Methyl
Bn: Benzyl
Pr: Propyl
iPr: isopropyl
Chx: Cyclohexyl
$^t$Bu: tert-Butyl
Ac: Acetyl
Ph: Phenyl Preparation of Intermediates Intermediate A:

Step 1:

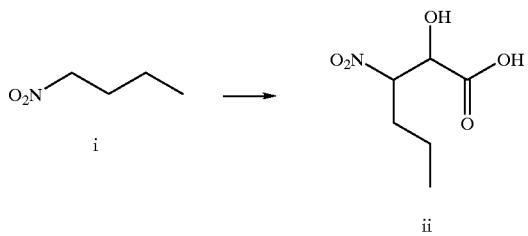

To a stirred solution of 1-nitrobutane (16.5 g, 0.16 mol) and glyoxylic acid in H$_2$O (28.1 g, 0.305 mol) and MeOH (122 mL) at 0° C.–5° C., was added dropwise triethyl amine (93 mL, 0.667 mol) over 2 hrs. The solution was warmed to room temperature, stirred overnight and concentrated to dryness to give an oil. The oil was then dissolved in H$_2$O and acidified to pH=1 with 10% HCl, followed by extraction with EtOAc. The combined organic solution was washed with brine, dried over Na$_2$SO$_4$, filtered and concentrated to dryness to give the product II (28.1 g, 99% yield).

Step 2:

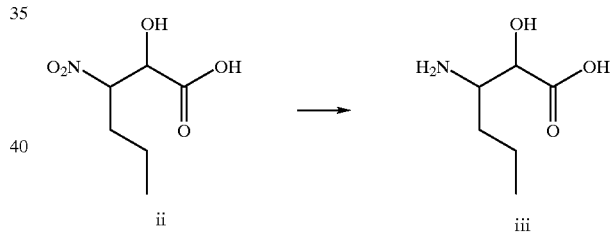

To a stirred solution of starting material ii (240 g, 1.35 mol) in acetic acid (1.25 L) was added 10% Pd/C (37 g). The resulting solution was hydrogenated at 59 psi for 3 hrs and then at 60 psi overnight. The acetic acid was then evaporated and azeotroped 3 times with toluene, then triturated with MeOH and ether. The solution was then filtered and azeotroped twice with toluene to give an off white solid (131 g, 0.891 mol, 66%).

Step 3:

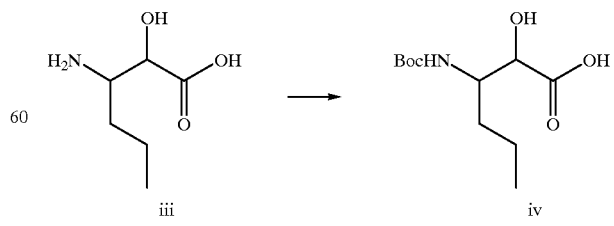

To a stirred solution of the amino acid iii (2.0 g, 13.6 mmol) in dioxane (10 mL) and H$_2$O (5 mL) at 0° C., was added 1N NaOH solution (4.3 mL, 14.0 mmol). The resulting solution was stirred for 10 minutes, followed by addition of di-t-butyidicarbonate (0.110 g, 14.0 mmol) and stirred at 0° C. for 15 minutes. The solution was then warmed to room temperature, stirred for 45 minutes and kept at refrigerator overnight and concentrated to dryness to give a crude material. To the solution of this crude material in EtOAc (100 mL) and ice, was added $KHSO_4$ (3.36 g) and $H_2O$ (32 mL) and stirred for 4–6 minutes. The organic layer was then separated and the aqueous layer was extracted twice with EtOAc and the combined organic layer was washed with water, brine, dried over $Na_2SO_4$, filtered and concentrated to dryness to give the product as a clear gum (3.0 g, 89% yield).

Step 4:

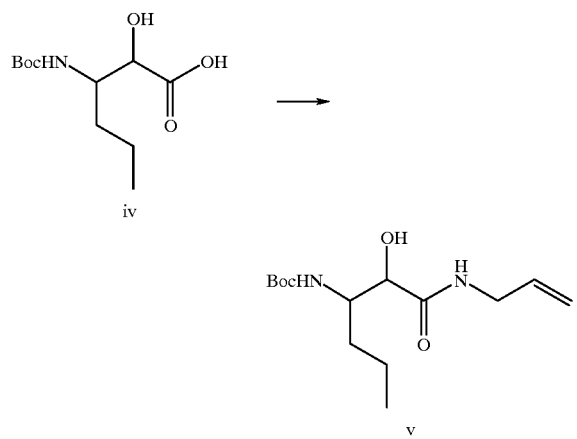

To a stirred solution of starting material iv (6.0 g, 24.3 mmol) in $CH_2Cl_2$ (120 mL) was added BOP reagent (12.9 g, 29.1 mmol), allyl amine (2.2 mL, 29.1 mmol) and $Et_3N$ (12.0 mL, 85.0 mmol). The resulting solution was stirred at room temperature overnight, then washed with 10% aq. citric acid, satd. $NaHCO_3$, and brine. The organic layer was dried over $Na_2SO_4$, concentrated to dryness and ran through column to give the product v (5.5 g, 80% yield).

Step 5:

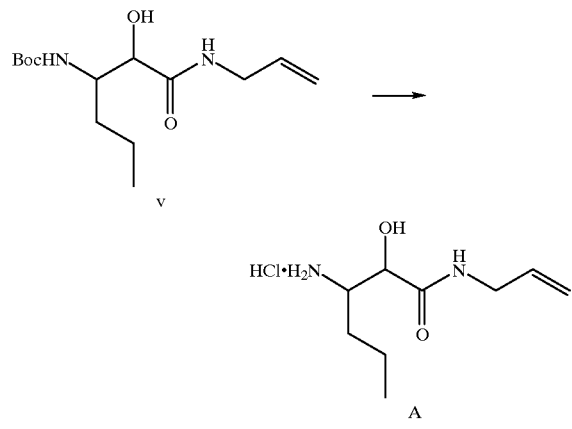

The solution of starting material v (2.1 g, 7.3 mmol) in 4M HCl/Dioxane (25 mL) was stirred at room temperature for 1 minute, then concentrated to dryness and dried overnight to give a crude product A (2.1 g, 100% yield).

Intermediate B

Step 1:

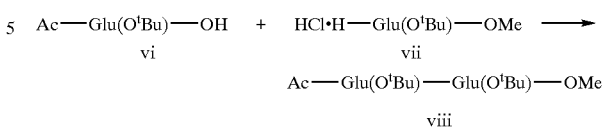

To a stirred solution of compound vi (4.83 g, 19.71 mmol) in dichloromethane (100 mL) at −20° C. was added HOOBt (3.38 g, 20.70 mmol), N-methylmorpholine (8.66 mL, 78.84 mmol) and EDCl (4.90 g, 25.62 mmol). The reaction mixture was stirred for 20 minutes, followed by the addition of vii (5.0 g, 19.71 mmol). The resulting solution was stirred at −20° to −10° C. for 45 min, then kept in the freezer overnight. The reaction mixture was washed twice with saturated $NaHCO_3$, 1N HCl, and brine, dried over $Na_2SO_4$, filtered and concentrated to dryness to give the product viii (8.2 g, 94% yield) which was sufficiently pure for further studies. LRMS m/z $MH^+$=445.1.

Step 2:

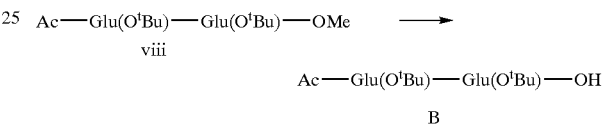

To a cold (0° C.) solution of viii (2.63 g, 5.92 mmol) in MeOH (30 mL) was added aqueous 1M LiOH solution (5.92 mL, 5.92 mmol). The reaction mixture was warmed to ambient temperature over 3.5 hrs when the starting material was completely consumed (by TLC). The solvent was removed and the residue was partitioned between EtOAc and aqueous $KHSO_4$(pH 3–4). The organic layer was separated, washed with brine, dried (MgSO4) and concentrated to afford 2.37 g (93%) of B, which was used in the subsequent step without purification. LRMS m/z $MH^+$= 431.3.

Intermediate C:

Step 1:

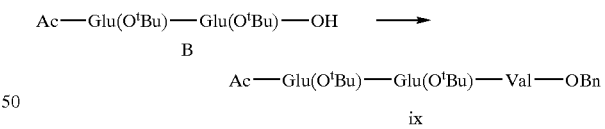

The starting material B was coupled with commercially available p-TsOH.H-Val-OBn using the procedure described for intermediate B, Step 1 to provide ix in 94% yield. The crude product was sufficiently pure for further studies. LRMS m/z $MH^+$=620.1.

Step 2:

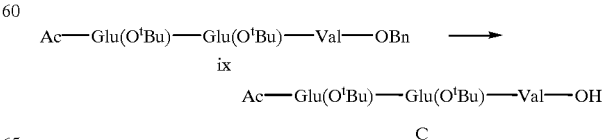

A solution of the starting material ix (1.35 g, 2.18 mmol) in absolute ethanol (20 mL) was stirred at ambient temperature under hydrogen atmosphere in the presence of Pd-C (30 mg, 10%) overnight. The mixture was filtered through a celite pad and the resulting solution was concentrated in vacuo to give the desired product C in quantitative yield. LRMS m/z MH$^+$=530.1.

Intermediate D:

Step 1:

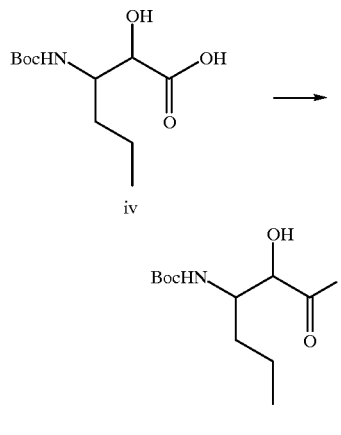

The desired compound iv was obtained by the procedure described for Intermediate A, Step 4 using p-TsOH.H-Gly-Oallyl as the coupling partner. Purification by column chromatography using 50/50 EtOAc/hexanes afforded pure iv in 85% yield. LRMS m/z MH$^+$=345.2.

Step 2:

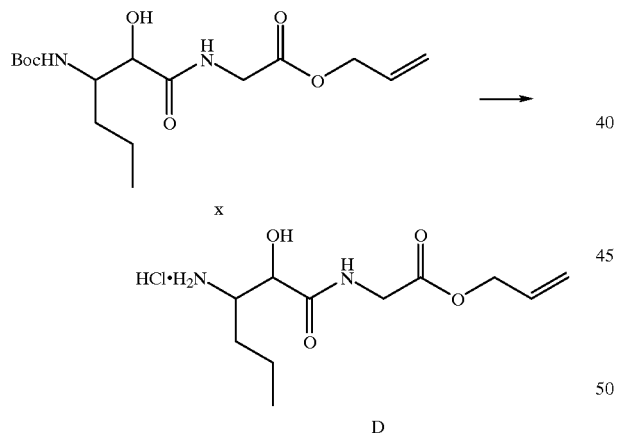

The desired intermediate D was obtained by the method described for Intermediate A, Step 5 (reaction time=1 hr). The crude material was used without further purification.

Intermediate E:

Step 1:

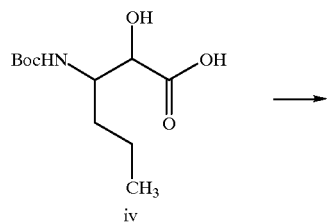

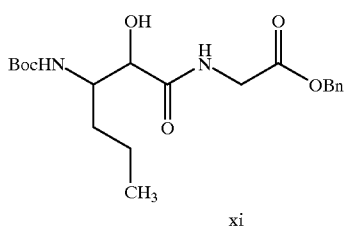

To a stirred solution of starting material (3.00 g, 12.0 mmol) in DMF (15 mL) and CH$_2$Cl$_2$ (15 mL) at −20° C. was added HOOBt (1.97 g, 12.0 mmol), N-methyl morpholine (4.0 mL, 36.0 mmol) and EDCl (2.79 g, 14.5 mmol) and stirred for 10 minutes, followed by addition of HCl.H$_2$N-Gly-OBn (2.56 g, 13.0 mmol). The resulting solution was stirred at −20° C. for 2 hrs, then kept at refrigerator overnight and concentrated to dryness, followed by dilution with EtOAc (150 mL). The EtOAc solution was then washed twice with saturated NaHCO$_3$, H$_2$O, 5% H$_3$PO$_4$, brine, dried over Na$_2$SO$_4$, filtered and concentrated to dryness to give the product (4.5 g, 94%). LRMS m/z MH$^+$=395.1.

Step 2:

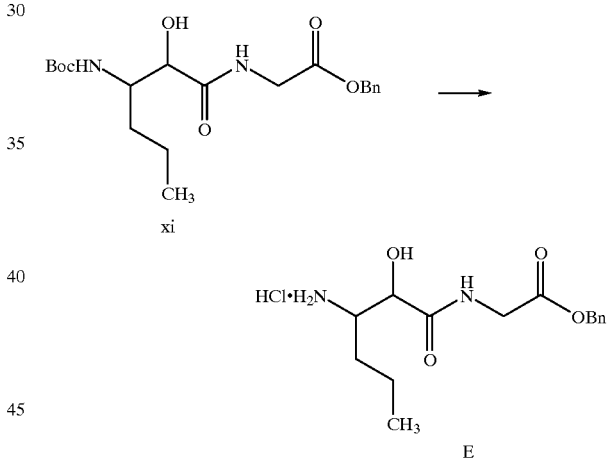

The desired intermediate E was prepared from compound xi according to the procedures described in Step 5 for intermediate A. It was used without further purification.

Intermediate F:

Step 1:

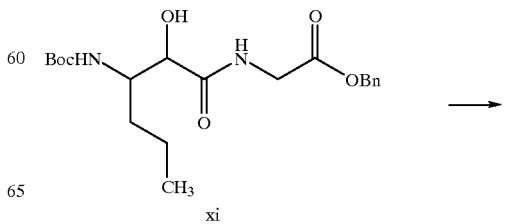

-continued

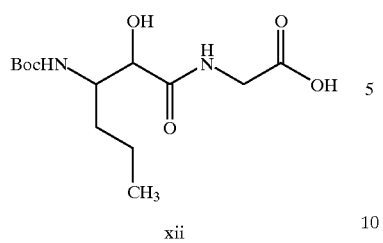

xii

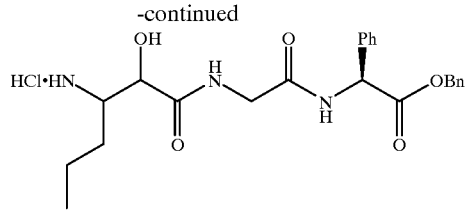

F

The desired product F was obtained by the procedure described for Intermediate A, Step 5. The crude material was used for further studies.

Intermediate G:

Step 1:

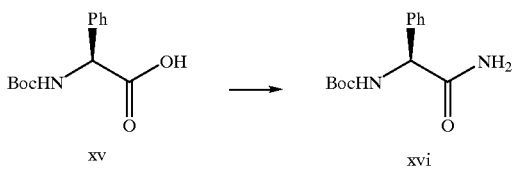

xv → xvi

The desired compound was synthesized by the procedure described for Intermediate E, Step 1 using commercially available xv and ammonium chloride. The crude residue was purified by column chromatography using 2.5/97.5 MeOH/dichloromethane to provide xvi in 44% yield. LRMS m/z MH$^+$=251.1.

Step 2:

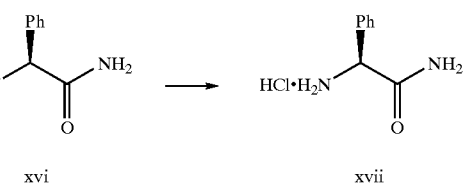

xvi → xvii

The desired compound xvii was obtained in quantitative yield using the procedure described for Intermediate A, Step 5. The crude material was used for further studies.

Step 3:

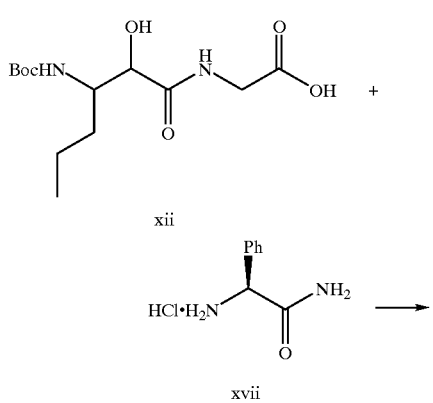

xii xvii →

The solution of starting material xi (7.00 g, 17.8 mmol) in absolute ethanol (300 mL) was stirred at room temperature under a hydrogen atmosphere in the presence of Pd-C (300 mg, 10%). The reaction progress was monitored by tlc. After 2h, the mixture was filtered through a celite pad and the resulting solution was concentrated in vacuo to give the product xii (5.40 g, quantitative). LRMS m/z MH$^+$=305.1.

Step 2:

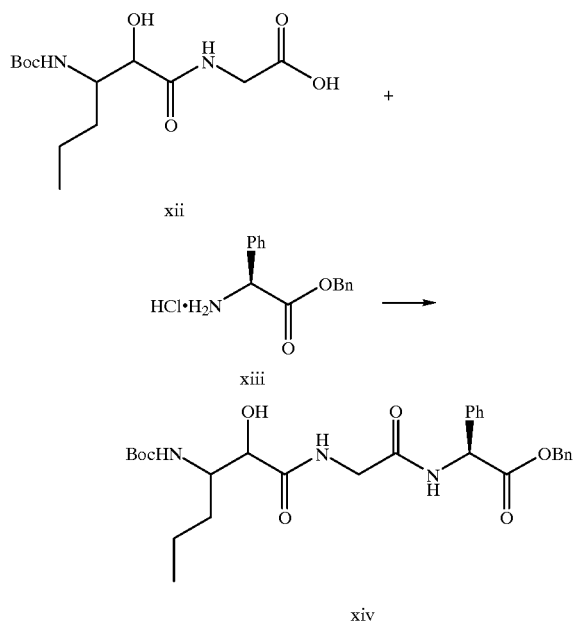

xii + xiii → xiv

The desired product xiv was obtained by the procedure described for Intermediate B, Step 1 using commercially available xiii as the coupling partner. The crude material was sufficiently pure for further studies.

Step 3:

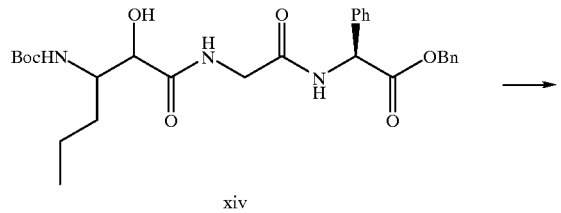

xiv →

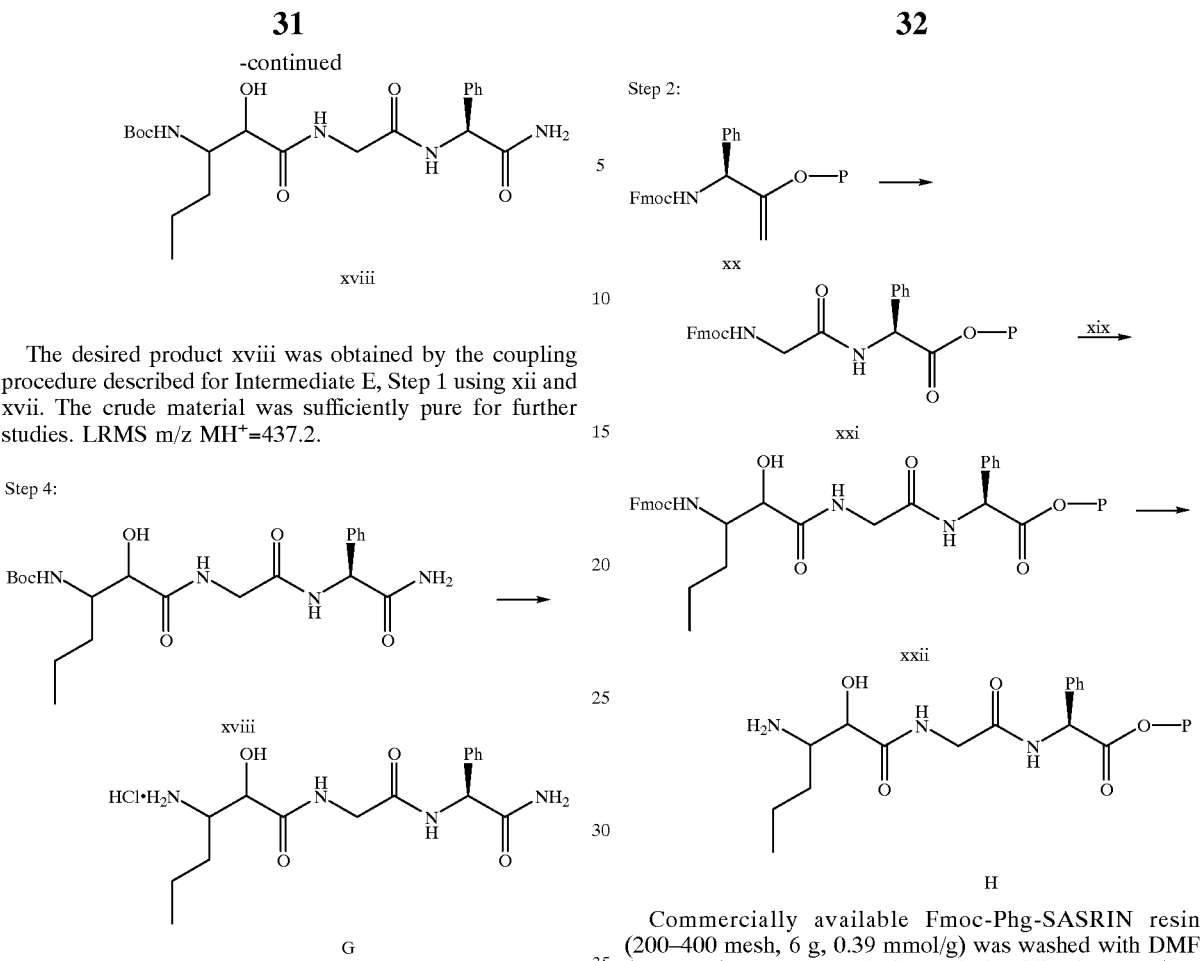

The desired product xviii was obtained by the coupling procedure described for Intermediate E, Step 1 using xii and xvii. The crude material was sufficiently pure for further studies. LRMS m/z MH$^+$=437.2.

Step 4:

The desired intermediate G was obtained from xviii using the procedure described for Intermediate A, Step 5 in quantitative yield. The crude material was used for further studies without purification.

Intermediate H:

Step 1:

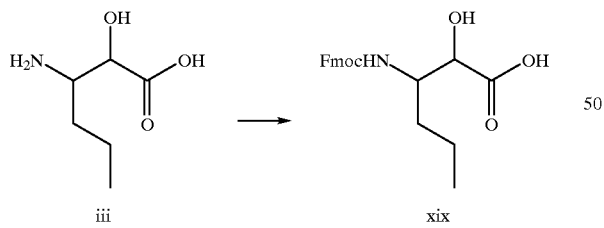

The starting material iii (21.5 g, 122 mmol) was dissolved in a solution of sodium carbonate (40.76 g) in water (625 mL). Dioxane (200 mL) was added. Fmoc-OSu (Fmoc-succinimide, 40.15 g, 121 mmol) in dioxane (400 mL) was added and the reaction mixture was stirred at ambient temperature overnight. Water (1000 mL) was added and washed with ether (6 times) to remove any unreacted Fmoc-OSu. The aqueous layer was acidified (conc. HCl) and extracted with EtOAc. The organic layer was washed with 1N HCl, dried (Na$_2$SO$_4$), filtered and concentrated to afford xix in quantitative yield.

Step 2:

Commercially available Fmoc-Phg-SASRIN resin (200–400 mesh, 6 g, 0.39 mmol/g) was washed with DMF (2×90 mL). It was treated with 20% piperidine in DMF (v/v, 100 mL) for 30 min, followed by washing with DMF (4×90 mL). DMF (90 mL) was added to the resin followed by Fmoc-Gly-OH (2.09 g, 7.02 mmol), HATU (2.67 g, 7.02 mmol) and DIPEA (2.45 mL, 14.04 mmol). After shaking at ambient temperature overnight, the resin was washed with DMF (4×90 mL) to afford resin-bound compound xxi.

The above described sequence of Fmoc deprotection and coupling (with xix instead of Fmoc-Gly-OH, reaction time=4 hrs) was repeated to afford resin-bound compound xxii. The required intermediate H was obtained by treating xxii with 20% v/v piperidine in DMF as explained before. This material was stored in the refrigerator prior to use.

EXAMPLES

Examples 1

Preparation of compound of Formula 1

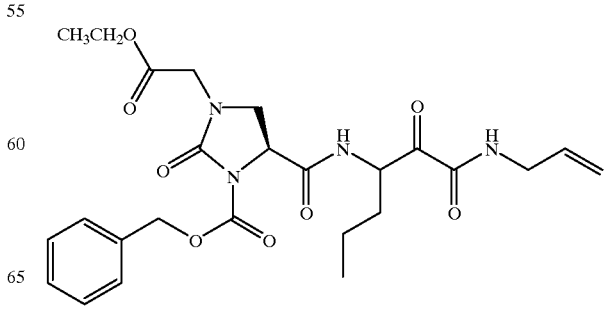

Step A:

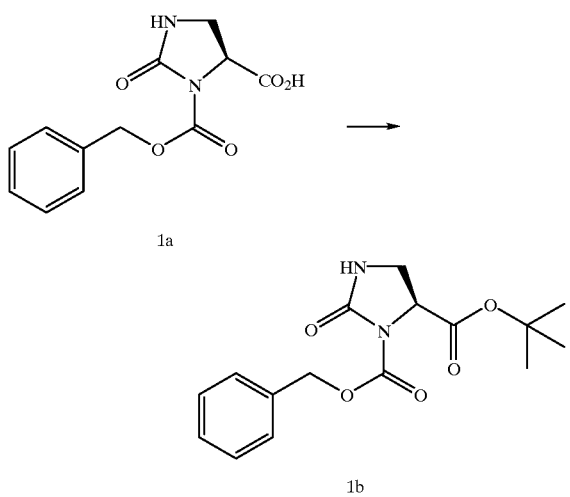

A solution of compound 1a (10.0 g, 37.8 mmol) in pyridine (18 mL), t-BuOH (14 mL) and CHCl₃ (25 mL) was cooled at −15° C. for 10 minutes, followed by dropwise addition of phosphorous oxychloride (4 mL). The resulting solution was stirred at −15° C. for 30 minutes, then warmed to room temperature for 4 hrs. The solution was then washed with $H_2O$, 1% cold HCl, saturated $NaHCO_3$, and brine. The combined organic layer was dried over $Na_2SO_4$, concentrated to dryness and purified by column chromatography on silica gel, eluting with 35% EtOAc/65% $CH_2Cl_2$ to give compound 1b (11.0 g, 91% yield).

Step B:

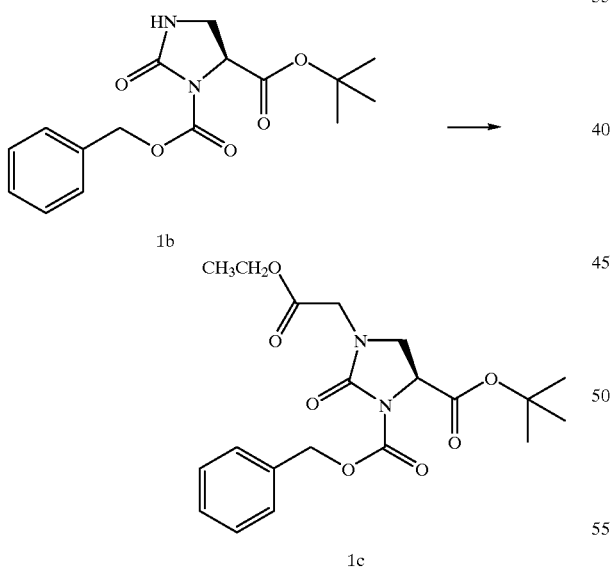

To a stirred solution of compound 1b (2.45 g, 15.2 mmol) in DME (35 mL) was added $K_2CO_3$ (2.1 g, 15.2 mmol), $EtO_2C$—$CH_2Br$ (3.4 mL, 30.7 mmol) and a small amount of tetra-n-butylammonium iodide. The resulting solution was stirred at room temperature overnight and concentrated to dryness, followed by extraction with EtOAc-brine. The combined organic layer was dried over $Na_2SO_4$, then concentrated to dryness and purified by column chromatography, eluting with 25% EtOAc/75% $CH_2Cl_2$ to give compound 1c (2.06 g, 66% yield).

Step C:

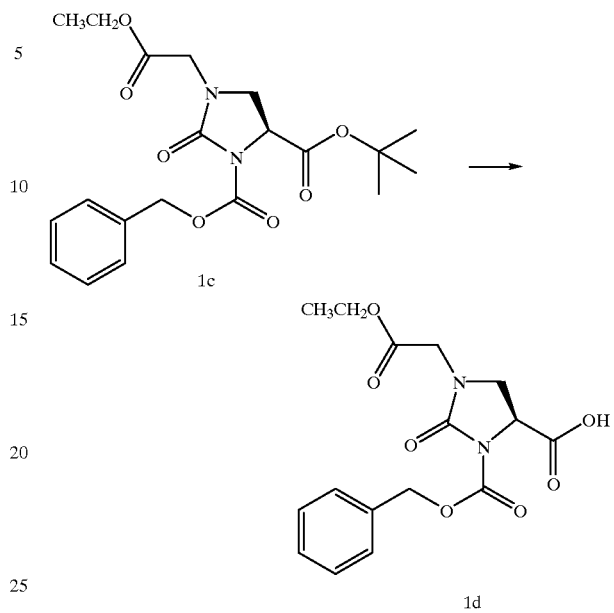

To a stirred solution of starting material 1c (1.0 g, 2.46 mmol) was added TFA (4.0 mL, 2.46 mmol). The resulting solution was stirred at room temperature for 1 hr, concentrated to dryness and dried overnight to give compound 1d (0.88 g, 100% yield).

Step D:

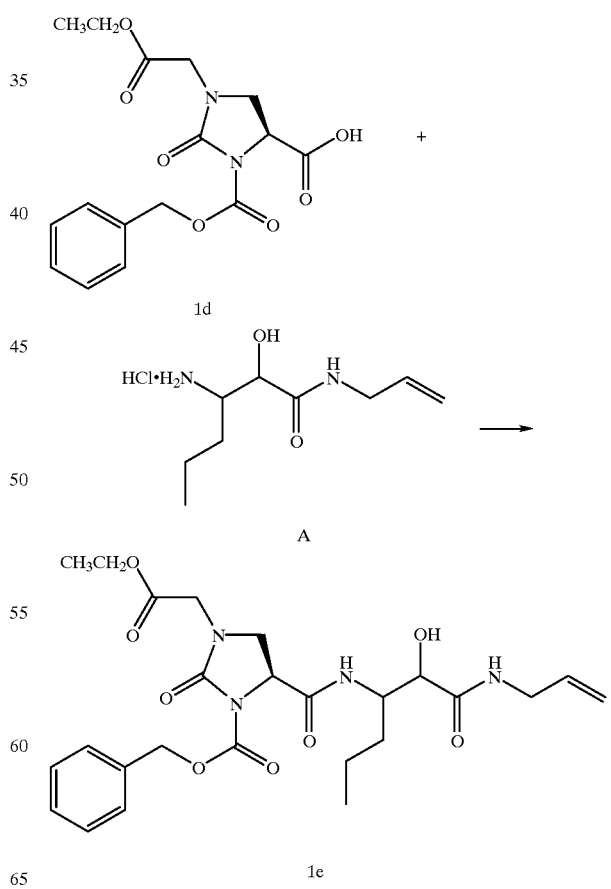

To a stirred solution of starting material 1d (0.3 g, 0.857 mmol) in CH$_2$Cl$_2$ (15 mL) was added A (0.19 g, 0.857 mmol), BOP reagent (0.42 g, 0.94 mmol) and Et$_3$N (0.42 mL, 3.0 mmol). The resulting solution was stirred at room temperature overnight, then washed with 10% aqueous citric acid, saturated NaHCO$_3$, and brine. The combined organic layer was dried over Na$_2$SO$_4$, concentrated to dryness and then ran through column to give compound 1e (0.15 g, 34% yield).

Step E:

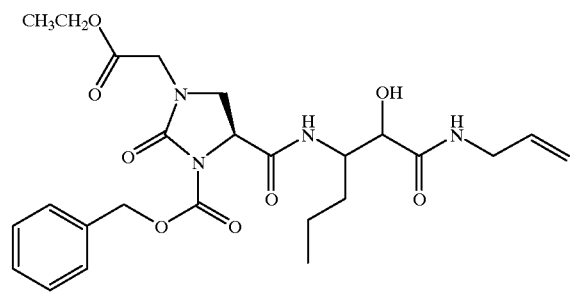

1e

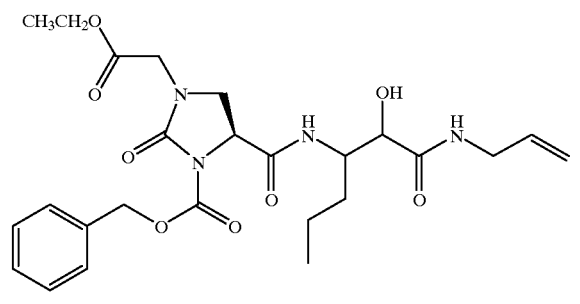

1

To a stirred cooling solution of compound 1e (0.1 g, 0.193 mmol) in CH$_2$Cl$_2$ (10 mL) at 0° C., was added Dess-Martin's oxidant (0.123 g, 0.289 mmol). The resulting solution was stirred at room temperature for 1 hour, then poured into aq. Na$_2$S$_2$O$_3$ (15 mL), satd. NaHCO$_3$ (15 mL) and CH$_2$Cl$_2$ (15 mL) with ice and stirred at room temperature for half an hour. The solution was then concentrated to dryness and purified by prep TLC using 5% MeOH/95% CH$_2$Cl$_2$ to give the final product, compound 1 (90 mg, 91% yield). HRMS (FAB) Calcd for C$_{25}$H$_{33}$N$_4$O$_8$: 517.2298 (M+H)$^+$. Found: 517.2307.

Example 2

Preparation of Compound of Formula 2

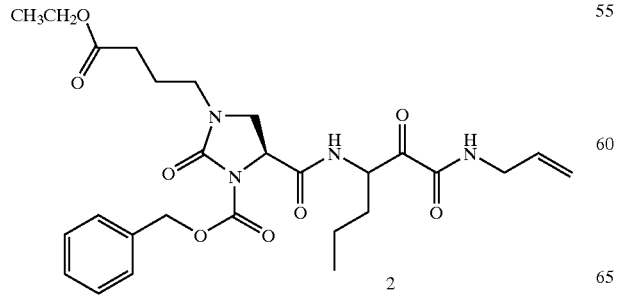

2

Step A:

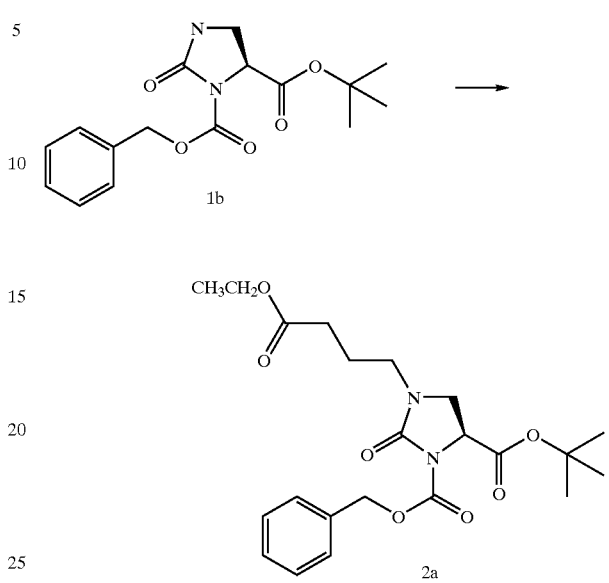

1b

2a

The desired product 2a was prepared in 60% isolated yield, as described above for Example 1, Step B, using ethyl-4-bromobutyrate as the alkylating agent.

Step B:

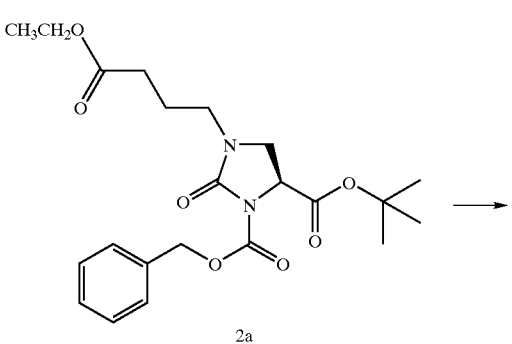

2a

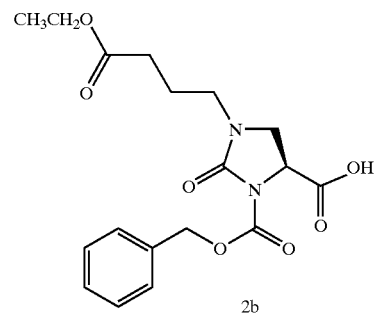

2b

The desired product 2b was prepared in quantitative yield, as described above for Example 1, Step C.

Step C:

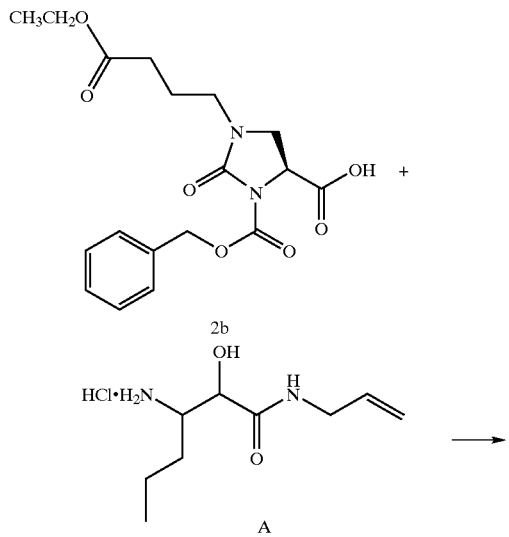

To a stirred solution of starting material 2b (0.174 g, 0.46 mmol) in CH$_2$Cl$_2$ (5 mL) was added A (0.113 g, 0.51 mmol), EDCl (0.106 g, 0.552 mmol), HOBt (0.085 g, 0.552 mmol) and NMM (0.177 mL, 1.61 mmol). The resulting solution was stirred at −20° C. for 48 hrs. The solution was then washed with satd. NaHCO$_3$, 10% aq. citric acid and brine. The combined organic layer was dried over Na$_2$SO$_4$ and purified by column chromatography using 5/95 MeOH/CH$_2$Cl$_2$ to give product 2c (0.082 g, 71% yield, MH$^+$= 547.3).

Step D:

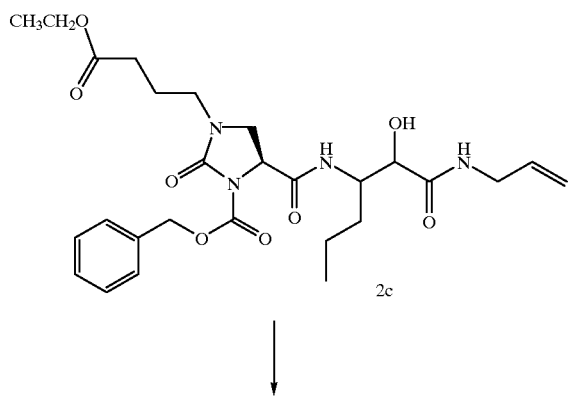

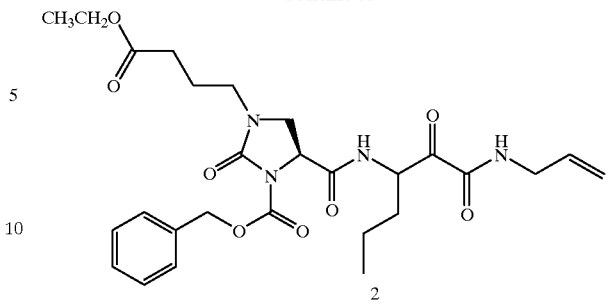

The desired product 2 was prepared in 78% isolated yield, as described above for Example 1, Step E. HRMS (FAB) Calcd for C$_{27}$H$_{37}$N$_4$O$_8$: 545.2611 (M+H)$^+$. Found: 545.2607.

Example 3

Preparation of Compound of Formula 3

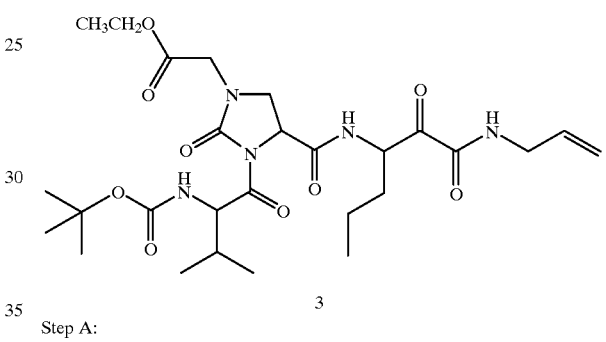

Step A:

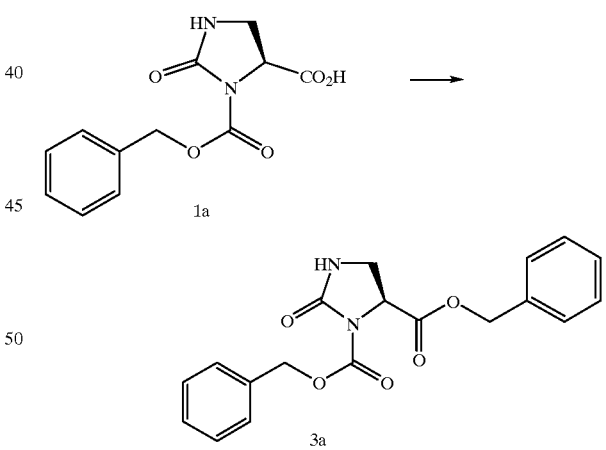

To the starting material 1a (10.50 g, 39.74 mmol) in benzene (100 mL) was added benzyl alcohol (10.30 mL, 99.35 mmol) and p-toluenesulfonic acid (1.52 g, 7.95 mmol). The reaction mixture was refluxed overnight. It was then cooled to room temperature and washed with saturated NaHCO$_3$ solution and brine. The organic layer was separated, dried (Na$_2$SO$_4$) and concentrated. The residue was dissolved in minimum amount of EtOAc and then hexanes was added to this solution. The white solid which crashed out was filtered and dried to give 8.2 g (58%) of pure product 3a.

Step B:

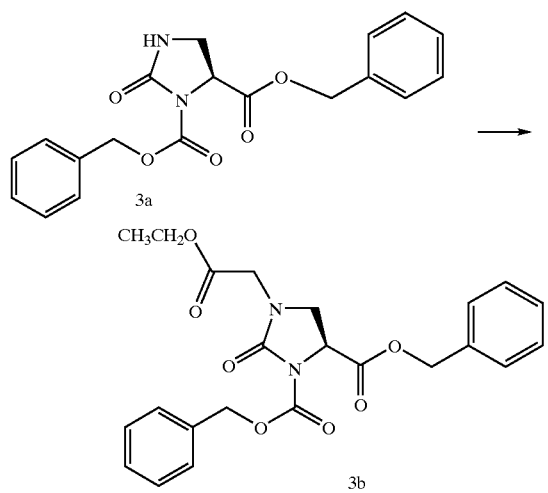

The desired product 3b was obtained from 3a using the procedure described for Example 1, Step B. Purification of the crude material using 10/90 EtOAc/dichloromethane provided 3b in 74% yield.

Step C:

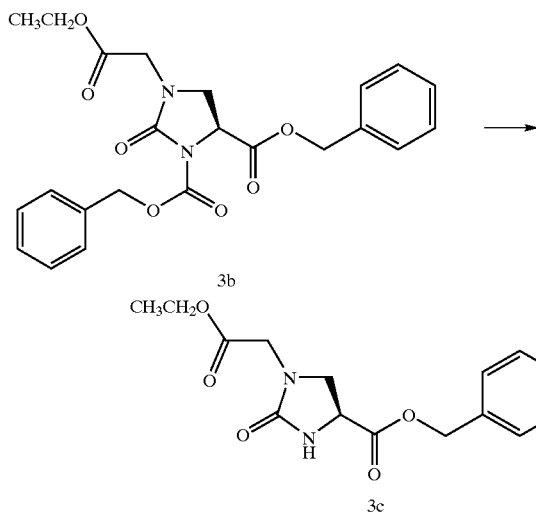

A solution of 3b (1.29 g, 2.93 mmol) in 30% HBr in AcOH (5 mL) was stirred at ambient temperature for 20 min. It was then poured slowly into a stirred solution of ice/ saturated NaHCO$_3$ and extracted with EtOAc. The organic layer was separated, dried (Na$_2$SO$_4$) and concentrated. Purification by flash column chromatography using 30/70 to 50/50 EtOAc/dichloromethane provided 632 mg (70%) of 3c.

Step D:

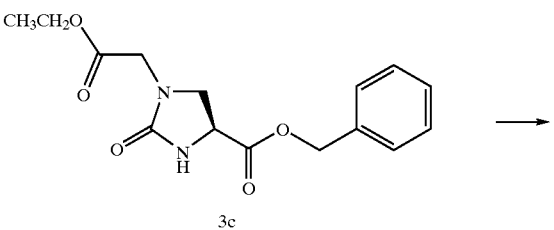

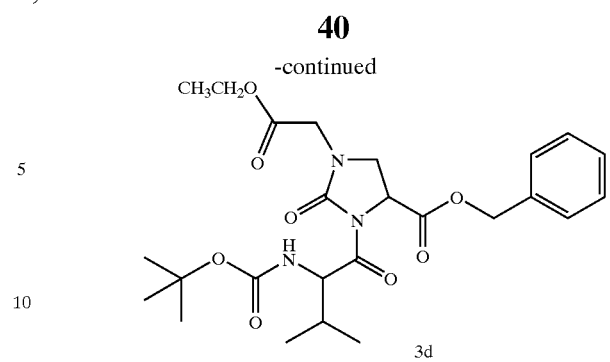

To a solution of N-Boc-valine (424 mg, 1.95 mmol) and N-hydroxysuccinimide (230 mg, 2.0 mmol) in THF (8 mL) at 0°–5° C. was added DCC (413 mg, 2.0 mmol). The reaction mixture was slowly warmed to ambient temperature overnight. The solid was filtered off and the filtrate was concentrated. The crude N-Boc-valine succinimide ester was used further without purification.

To a cold (−50° C.) solution of 3c (600 mg, 1.96 mmol) in THF (5 mL) was added potassium tert-butoxide (220 mg, 1.96 mmol) and warmed to −20° C. over 20 minutes. To this mixture was added a slurry of the crude N-Boc-valine succinimide ester (described above) in THF (4 mL) and warmed to −10° C. over 20 minutes. The reaction was quenched with saturated ammonium chloride solution and extracted with EtOAc. The organic layer was separated, dried (Na$_2$SO$_4$) and concentrated. Purification by flash column chromatography using 5/95 to 10/90 EtOAc/ dichloromethane provided 543 mg (55%) of 3d as a mixture of diastereomers.

Step E:

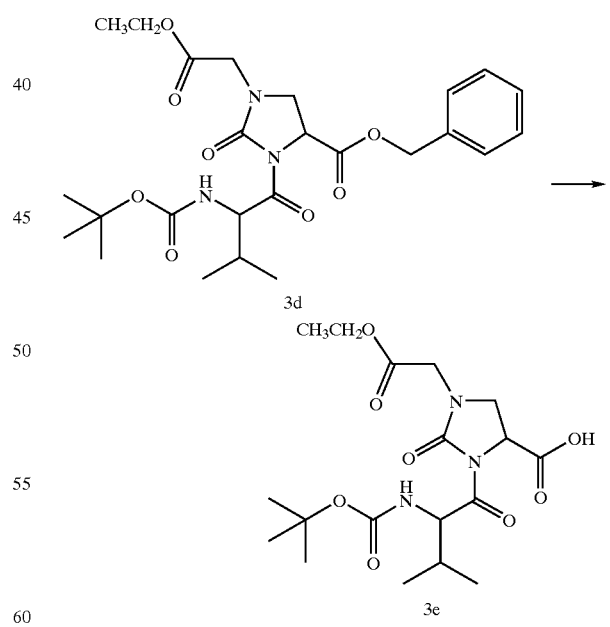

To a solution of 3d (525 mg, 1.04 mmol) in EtOH (8 mL) was added 5% palladium on carbon. The suspension was stirred under hydrogen atmosphere for 2 hrs. The catalyst was filtered off through a pad of celite and the filtrate was concentrated to provide 3e in quantitative yield.

Step F:

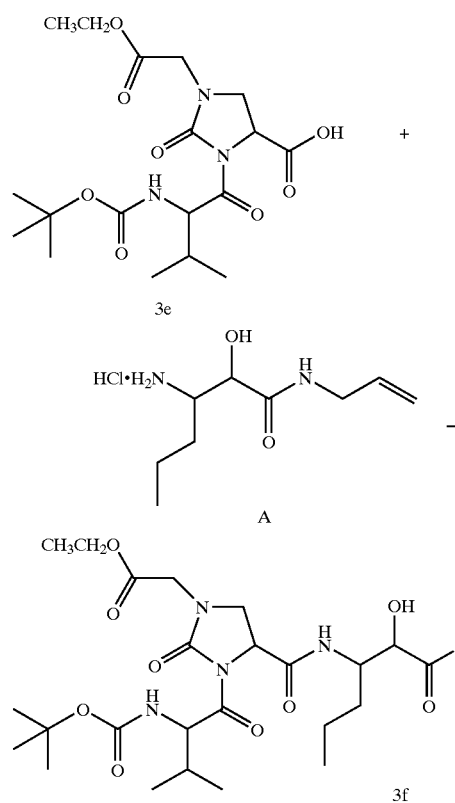

The expected product 3f was obtained by the protocol described above for Example 2, step C. Purification by flash column chromatography using 5/95 MeOH/dichloromethane provided 3f in 47% yield as a mixture of diastereomers.

Step G:

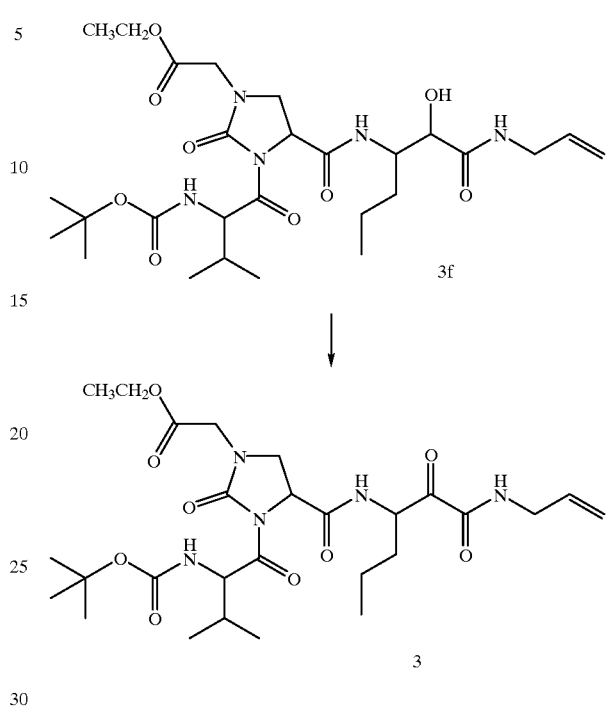

The desired product 3 was prepared in 67% isolated yield, as described above for Example 1, Step E.

Example 4

Preparation of Compound of Formula 4

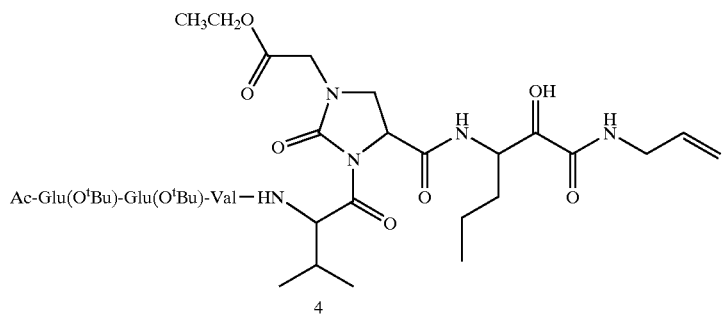

Step A:

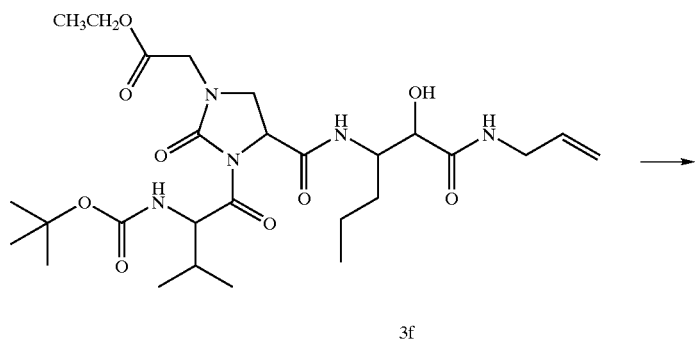

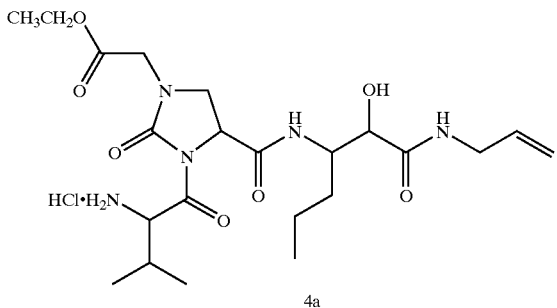

4a

4N HCl in dioxane (5 mL) was added to 3f (200 mg, 0.343 mmol) and cooled to 0° C. The reaction mixture was slowly warmed to ambient temperature over 3 hrs. It was then concentrated and dried overnight to provide 4a in quantitative yield, which was used without purification.

Step B:

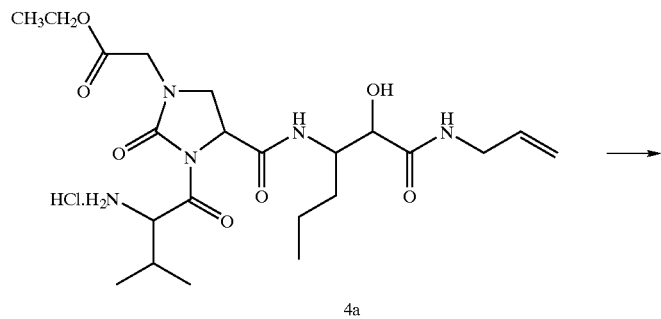

4a

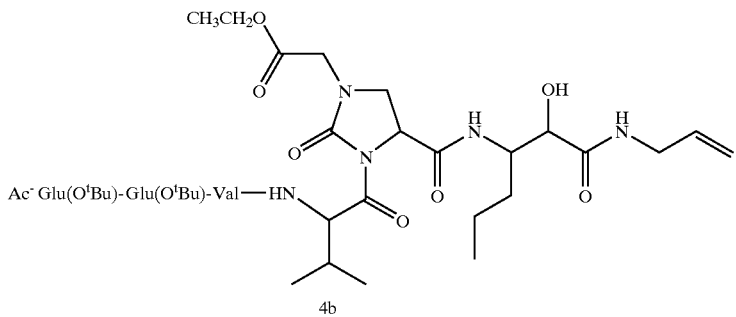

4b

To a cold (−20° C.) solution of 4a (110 mg, 0.21 mmol) and C (111 mg, 0.21 mmol) in anhydrous dichloromethane (4 mL) was added EDCl (48 mg, 0.252 mmol), HOOBt (41 mg, 0.252 mmol) and NMM (0.06 mL, 0.525 mmol). After being stirred at this temperature for 2 days the reaction mixture was diluted with dichloromethane and washed with saturated NaHCO$_3$, 10% aqueous citric acid, and brine. It was dried over sodium sulfate, filtered and concentrated in vacuo. Flash chromatography (6/94 MeOH/dichloromethane) afforded 4b (169 mg) in 81% yield.

Step C:
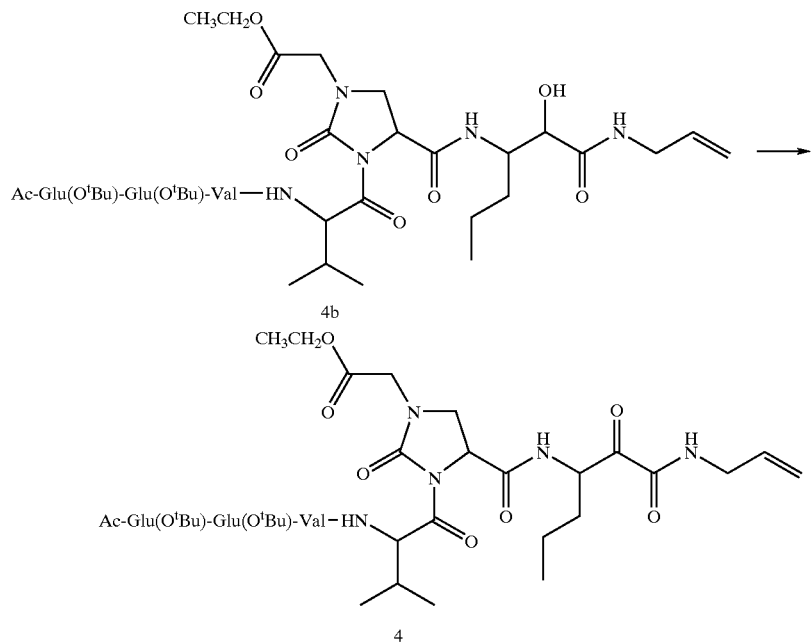
The desired product 4 was obtained by the oxidation of 4b in 73% isolated yield, as described above for Example 1, Step E.
Example 5
Preparation of Compound of Formula 5
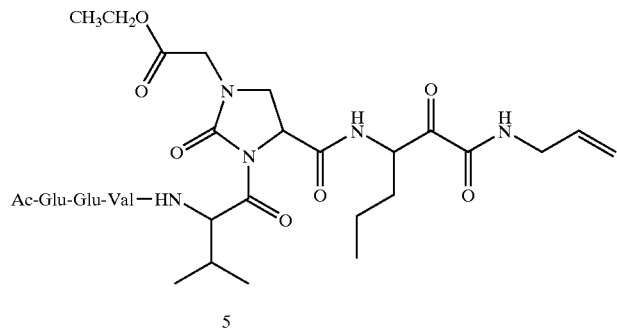
Step A:
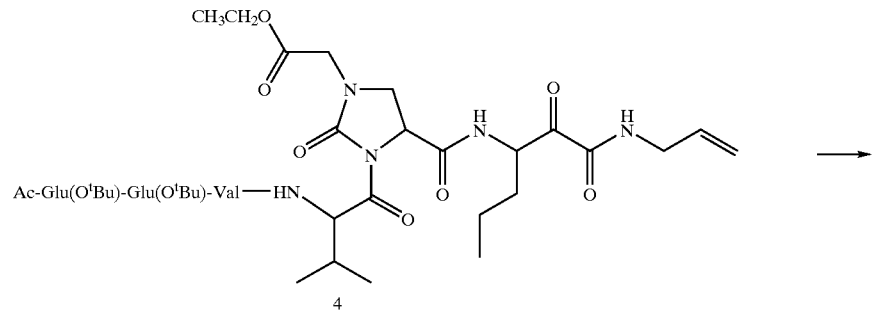

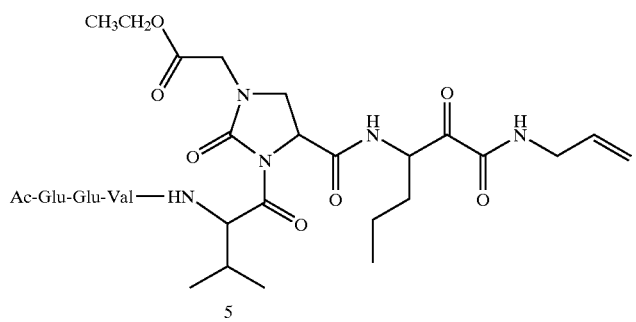

The desired product 5 was prepared in quantitative yield, as described above for Example 4, Step A.

The following compounds (6–8) shown in Table 2 were prepared by essentially the above described procedures using aminoacid derivatives from commercial or literature sources.

TABLE 2

| Compound | X$^1$ | M + H (HRMS) |
|---|---|---|
| 3 | Boc-Val- | 582.3133 |
| 4 | Ac-Glu(O$^t$Bu)-Glu(O$^t$Bu)-Val- | 993.5470 |
| 5 | Ac-Glu-Glu-Val- | 881.4263 |
| 6 | Ac-Glu(O$^t$Bu)- | 709.3776 |
| 7 | Ac-Glu- | 653.3156 |
| 8 | iBoc-Val- | 681.3822 |

Examples 9–14

Preparation of Compounds of Formulae 9–14

Scheme 1

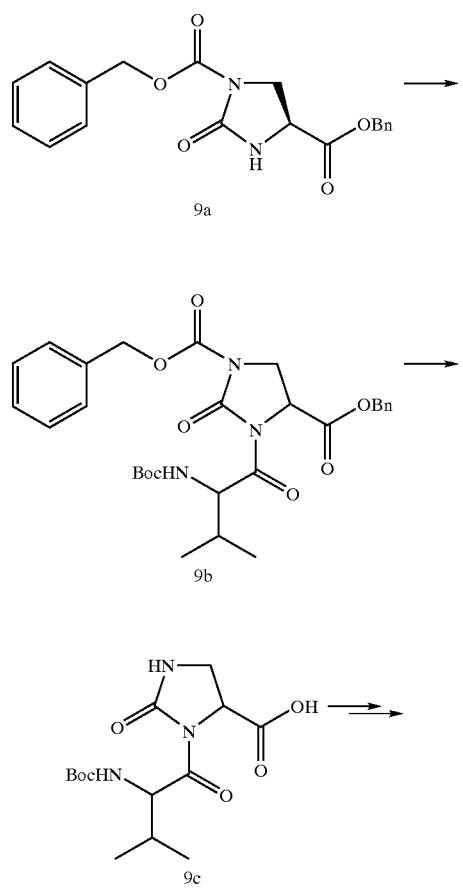

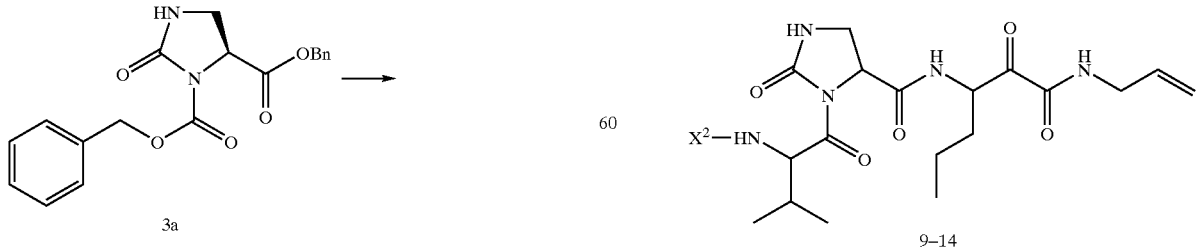

TABLE 3

| Compound | X² | M + H (HRMS) |
|---|---|---|
| 9 | Boc-Val- (isomer 1) | 595.3463 |
| 10 | Boc-Val- (isomer 2) | 595.3463 |
| 11 | Ac-Glu(O$^t$Bu)-Glu(O$^t$Bu)-Val- | 907.5120 |
| 12 | Ac-Glu-Glu-Val- | 795.3889 |
| 13 | Boc | 496.2779 |
| 14 | H | 396.2247 |

Synthesis of 9a: To a cold (0° C.) solution of 3a (2.0 g, 5.65 mmol) in THF (25 mL) was added NaH (60% dispersion in oil, 264 mg, 6.6 mmol) in two portions. Slowly warmed the reaction mixture to 10° C. over 2 hrs. It was quenched with aqueous 10% citric acid solution and brine and extracted into EtOAc. The organic layer was dried over sodium sulfate, filtered and concentrated. The crude material was purified by flash chromatography using 3/97 MeOH/dichloromethane. The material obtained was triturated with minimum amount of ether and filtered. The solid was dried under vacuum overnight to provide pure 9a (1.31 g) in 66% yield as a white solid.

Synthesis of 9b: The required product 9b was synthesized using the procedure described for Example 3, Step D in 80% yield, after purification by flash chromatography, as a white foam.

Synthesis of 9c: The required product 9c was obtained using the procedure described for Example 3, Step E (reaction time—overnight) in quantitative yield as a white foam.

The compounds (9–14) shown in Table 3 were prepared by procedures described previously.

Examples 15–18

Preparation of Compounds of Formulae 15–18

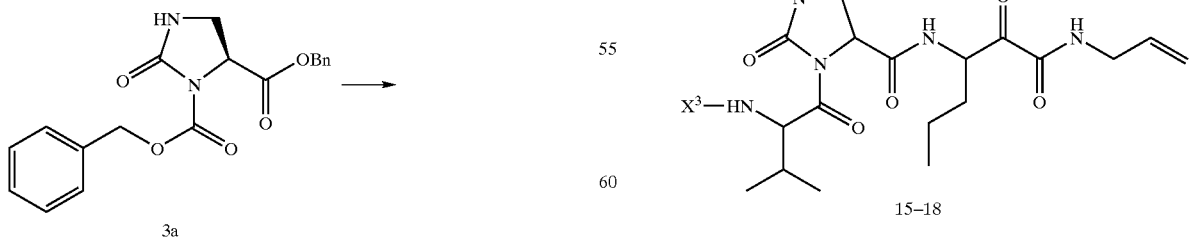

TABLE 4

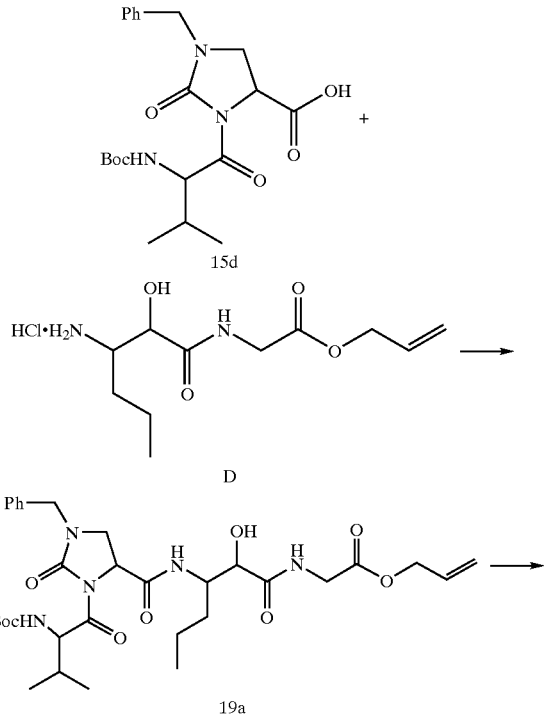

| Compound | X³ | M + H (NRMS) |
|---|---|---|
| 15 | Boc-Val- | 685.3900 |
| 16 | Val- | 585.3401 |
| 17 | Ac-Glu(O'Bu)-Glu(O'Bu)-Val- | 997.5631 |
| 18 | Ac-Glu-Glu-Val- | 885.4359 |

Synthesis of 15c: The starting material 3a was converted to 15a and then to 15b using the literature described procedure (K. Hayashi et. al., *J. Med. Chem.*, 1989, 32, 289–297). The required product 15c was obtained from 15b by the procedure described for Example 3, Step D in 50% isolated yield.

Synthesis of 15d: The required product 15d was obtained using the procedure described for Example 3, Step E (reaction time—overnight) in quantitative yield.

The compounds (15–18) shown in Table 4 were prepared by procedures described previously.

Examples 19–25

Preparation of Compounds of Formulae 19–25

Scheme 3

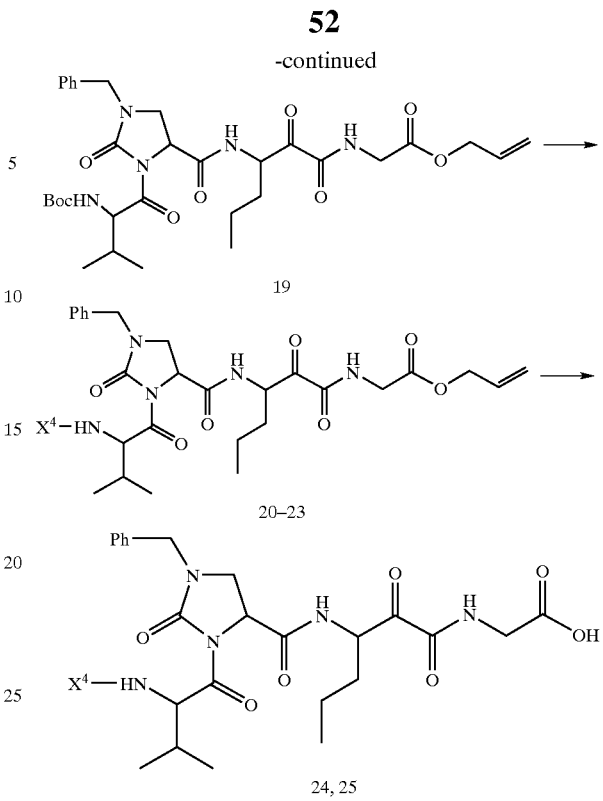

TABLE 5

| Compound | X⁴ | Y¹ | M + H (HRMS) |
|---|---|---|---|
| 19 | Boc- | allyl | 644.3308 |
| 20 | H | allyl | 544.2762 |
| 21 | Boc-Val- | allyl | 743.3990 |
| 22 | Ac-Glu(O'Bu)-Glu(O'Bu)-Val- | allyl | 1055.5617 |
| 23 | Ac-Glu-Glu-Val- | allyl | 943.4410 |
| 24 | Boc-Val- | H | 703.3680 |
| 25 | Ac-Glu(O'Bu)-Glu(O'Bu)-Val- | H | 1015.5353 |

Synthesis of 19a: The required compound 19a was prepared by the coupling reaction of 15d and intermediate D using the procedure described for Example 4, Step B in 64% isolated yield.

Synthesis of 19: The desired compound 19 was obtained by the oxidation protocol described previously for Example 1, Step E. The crude material was purified by flash column chromatography using 5/1 dichloromethane/EtOAc to provide 19 in 83% yield.

Synthesis of compounds 20–23: Preparation of these derivatives follow essentially previously described procedures.

Synthesis of compounds 24, 25: To a solution of the allyl ester (21 or 22, 0.12 mmol) in THF (4 mL) under nitrogen atmosphere was added morpholine (1.2 mmol) and tetrakis (triphenylphosphine)palladium(0) (0.012 mmol). The reaction mixture was kept in the refrigerator (−5° to −10° C.) overnight. The solvent was removed in vacuo. The residue was dissolved in dichloromethane and washed with 5% $H_3PO_4$, water and brine. The organic layer was dried over sodium sulfate, filtered and concentrated. Purification by preparative TLC using 5/95 MeOH/dichloromethane provided the required product 24 or 25 (25–40% yield).

Examples 26–29

Preparation of Compounds of Formulae 26–29

Scheme 4

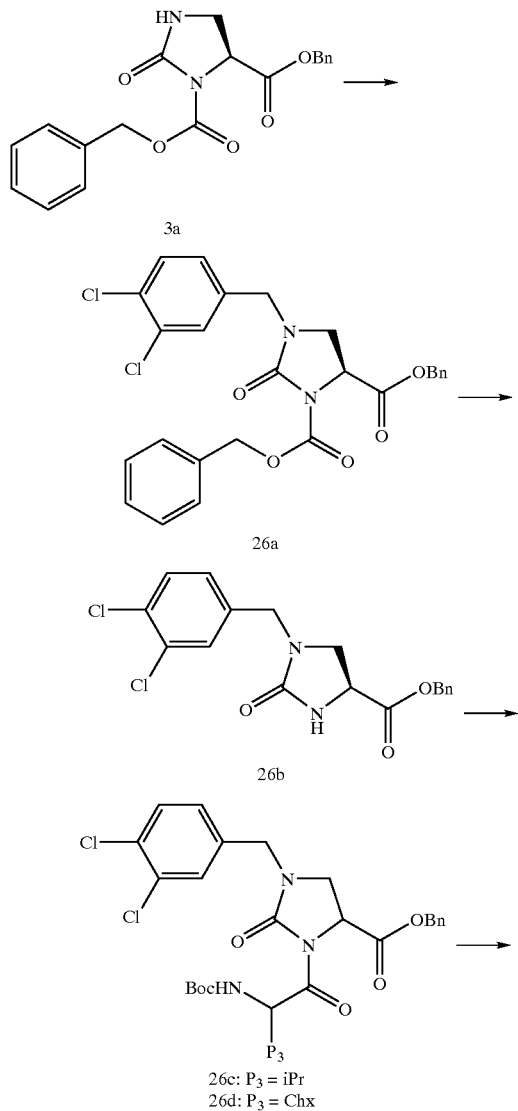

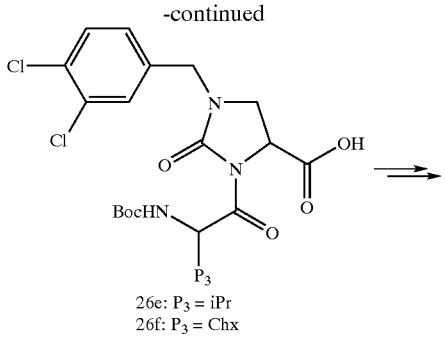

26e: $P_3$ = iPr
26f: $P_3$ = Chx

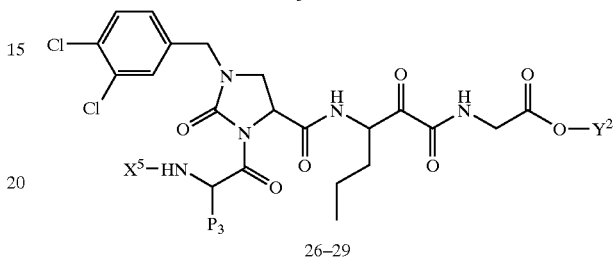

26–29

TABLE 6

| Compound | $X^5$ | $Y^2$ | $P_3$ | M + H (LC-MS) |
|---|---|---|---|---|
| 26 | Boc-Val- | allyl | iPr | 813.5 |
| 27 | Ac-Glu(O$^t$Bu)-Glu(O$^t$Bu)-Val- | allyl | iPr | 1125.3 |
| 28 | Ac-Glu-Glu-Val- | allyl | iPr | 1011.2 |
| 29 | Boc- | benzyl[a] | Chx | 702.1 (−100) |

[a]Prepared using intermediate E as the coupling partner with 26d.

Synthesis of 26a: The required material 26a was obtained from 3a and commercially available 3,4-dichlorobenzyl bromide using the procedure described for the synthesis of 15c (K. Hayashi et. al., *J. Med. Chem.*, 1989, 32, 289–297) in 83% yield after purification. HRMS (FAB) Calcd for $C_{26}H_{23}N_2O_5Cl_2$: 513.0984 (M+H)$^+$. Found: 513.0991.

Synthesis of 26b and 26c/d follow previously described procedures.

Synthesis of 26e: To a solution of 26c (1.25 g, 2.16 mmol) in EtOH (10 mL) was added 1M aqueous LiOH (3.02 mL, 3.02 mmol) and stirred at ambient temperature for 2 hrs. The reaction mixture was quenched with 10% aqueous citric acid solution (acidic by pH paper) and extracted with chloroform. The organic layer was dried (Na2SO4), filtered and concentrated to provide 26e. The crude material was used further without any purification. (26f was prepared by a similar procedure from 26d).

Synthesis of compounds 26–29 shown above (Table 6) follow essentially previously described procedures.

Examples 30–47

Preparation of Compounds of Formulae 30–47

General procedure for the N-benzylation of imidazolidinone 3a: The following imidazolidinone derivatives I-1 to I-10 (Table 7) were obtained by the N-alkylation of 3a and commercially available substituted benzyl bromide or chloride using the conditions described in literature (K. Hayashi et. al., *J. Med. Chem.*, 1989, 32, 289–297). In most cases the crude material after alkylation was sufficiently pure for further manipulation and were obtained in almost quantitative yield.

TABLE 7

| Compound | $Z^1$ | HRMS (Calcd/found) |
|---|---|---|
| I-1 | 4-bromo | 523.0869/523.0865 |
| I-2 | 3-bromo | 523.0869/523.0878 |

TABLE 7-continued

| Compound | $Z^1$ | HRMS (Calcd/found) |
|---|---|---|
| I-3 | 4-chloro | 479.1374/479.1370 |
| I-4 | 3-chloro | 479.1374/479.1374 |
| I-5 | 3,4-dimethyl | 473.2076/473.2088 |
| I-6 | 3-methyl | 459.1920/459.1908 |
| I-7 | 4-methyl | 459.1920/459.1917 |
| I-8 | 3-methoxy | 475.1869/475.1859 |
| I-9 | 4-methoxy | 475.1869/475.1873 |
| I-10 | 4-$^t$butyl | 501.2$^a$ |

$^a$LRMS data.

Scheme 5

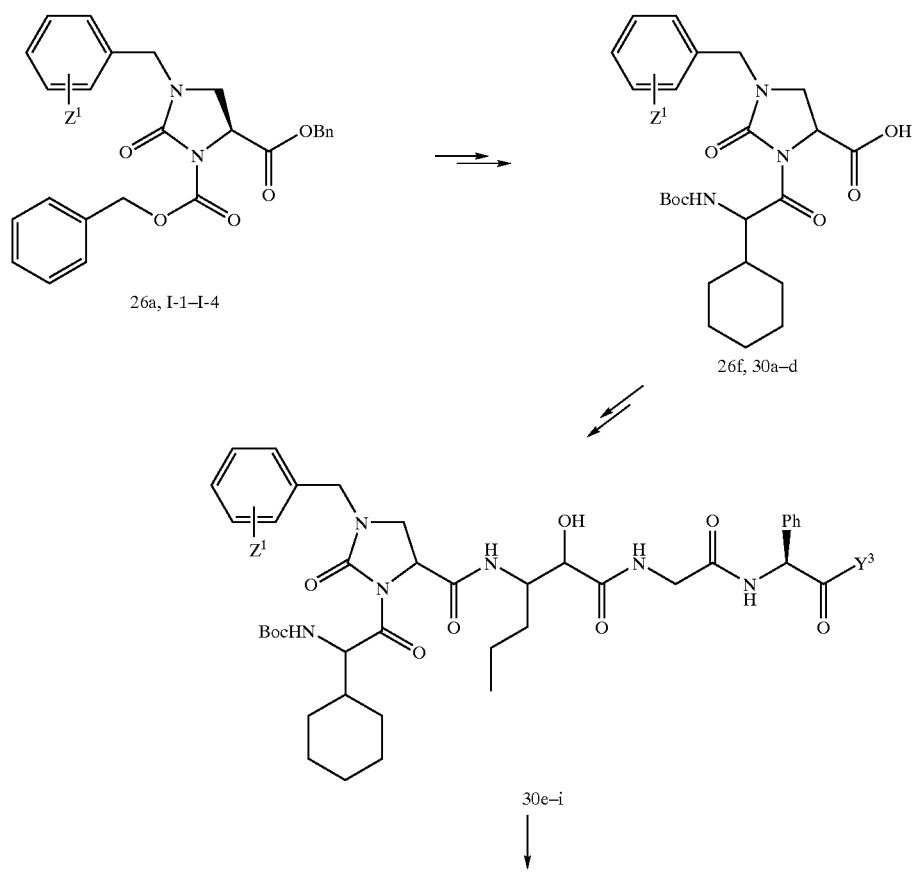

-continued
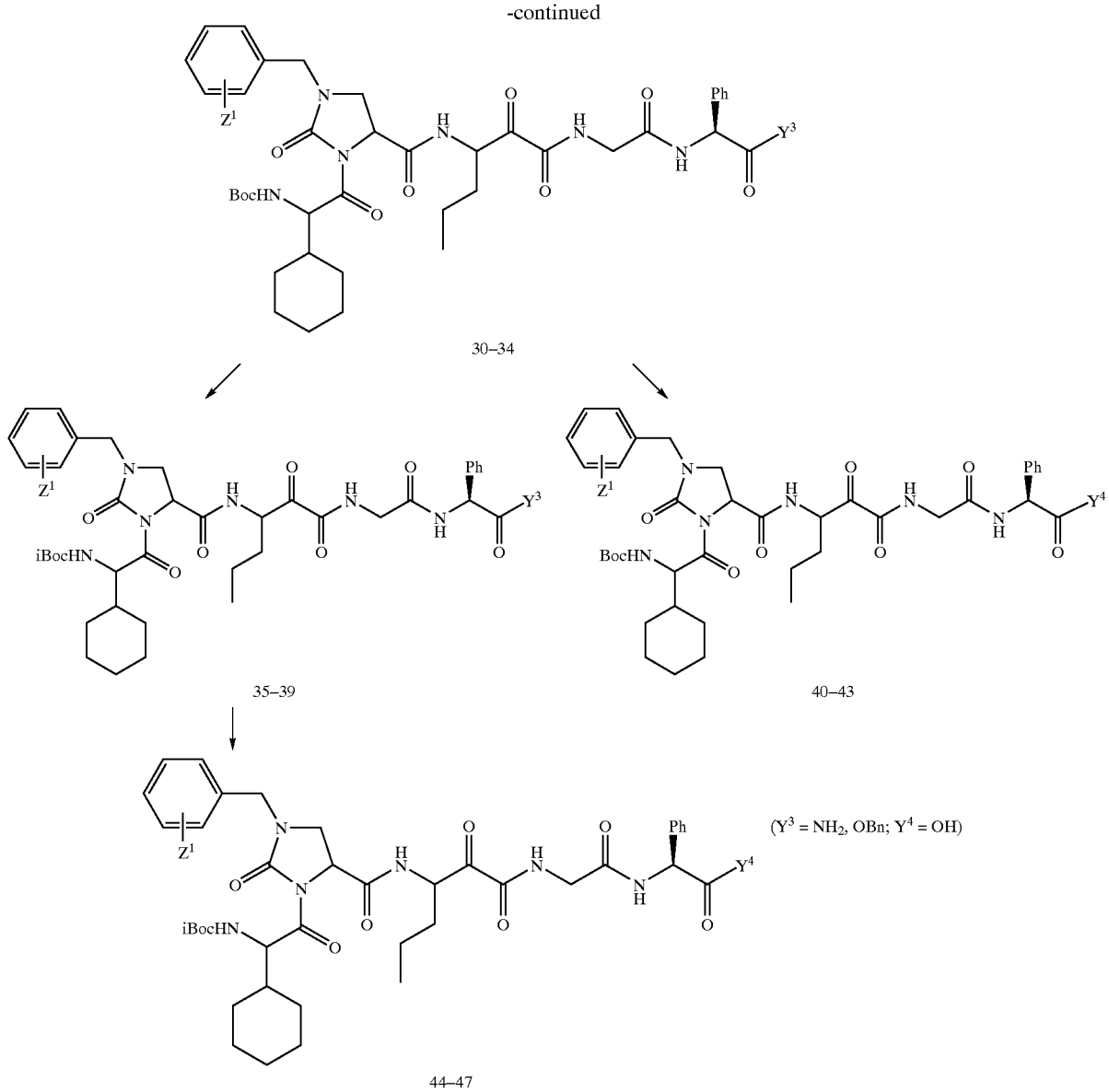
TABLE 8
| Compound | X6 | Z1 | Y5 | M + H (LC-MS) |
|---|---|---|---|---|
| 30 | Boc- | 3,4-dichloro | —NH2 | 844.2 |
| 31 | Boc- | 4-Bromo | —OBn | 947.3 |
| 32 | Boc- | 3-Bromo | —OBn | 947.3 |
| 33 | Boc- | 4-Chloro | —OBn | 901.3 |
| 34 | Boc- | 3-Chloro | —OBn | 901.2 |
| 35 | iBoc- | 3,4-dichloro | —NH2 | 844.2 |
| 36 | iBoc- | 4-Bromo | —OBn | 947.3 |
| 37 | iBoc- | 3-Bromo | —OBn | 947.3 |

TABLE 8-continued

[Structure shown with X⁶-HN, Z¹, Ph, Y⁵ substituents on a peptide scaffold]

| Compound | X⁶ | Z¹ | Y⁵ | M + H (LC-MS) |
|----------|------|---------|------|---------------|
| 38 | iBoc- | 4-Chloro | —OBn | 901.3 |
| 39 | iBoc- | 3-Chloro | —OBn | 901.3 |
| 40 | Boc- | 4-Bromo | —OH | 857.2 |
| 41 | Boc- | 3-Bromo | —OH | 857.2 |
| 42 | Boc- | 4-Chloro | —OH | 813.2 |
| 43 | Boc- | 3-Chloro | —OH | 813.2 |
| 44 | iBoc- | 4-Bromo | —OH | 857.2 |
| 45 | iBoc- | 3-Bromo | —OH | 857.2 |
| 46 | iBoc- | 4-Chloro | —OH | 813.2 |
| 47 | iBoc- | 3-Chloro | —OH | 813.2 |

Synthesis of 30e–i: The precursors (26f, I-1–I-4) were prepared by earlier describe protocol from appropriate building blocks. Coupling of these with intermediate F ($Y^3$=OBn) or G ($Y^3$=NH$_2$) independently using the EDCl/HOOBt/NMM procedure described previously provided the desired compounds 30e–i.

Synthesis of 30–34: The required compounds 30–34 were obtained by the oxidation procedure described for Example 1, Step E. Minimum amount of DMSO was added as cosolvent in cases were the starting material was not completely soluble in dichloromethane. Purification involved flash chromatography using MeOH (1–6%) in dichloromethane as the solvent system.

Synthesis of 35–39: The appropriate starting material (30–34, 0.1 mmol) was treated with 4M HCl in dioxane (3–5 mL) at 0° C. for 2 hrs. The reaction mixture was concentrated to afford the crude amine hydrochloride. This material was dissolved in THF (5 mL) and cooled to 0° C. To the cold solution was added triethylamine (0.44 mmol) and isobutylchloroformate (0.122 mmol). The reaction mixture was left in the freezer (~–8° C.) overnight. The solvent was evaporated and the residue was dissolved in EtOAc, washed with water, saturated NaHCO$_3$, saturated NH$_4$Cl and brine. The organic layer was dried (Na$_2$SO$_4$), filtered and concentrated to afford 35–39 which were homogeneous by TLC.

Synthesis of 40–47: To a solution of the appropriate starting material (31–34, 36–39, 0.05 mmol) in THF (3 mL) was added a solution of K$_2$CO$_3$ (0.06 mmol) in water (3 mL). If required, THF (1 mL) was added to obtain a homogeneous solution. t-Butanol (0.1 mL) was added after one hr and the reaction mixture was stirred at ambient temperature till completion (few hrs to 2 days). The reaction was quenched with 10% aqueous citric acid (acidic by pH paper) and extracted into dichloromethane. The organic layer was dried (Na$_2$SO$_4$), filtered and concentrated to afford 40–47.

Examples 48–57

Preparation of Compounds of Formulae 48–57

Scheme 6

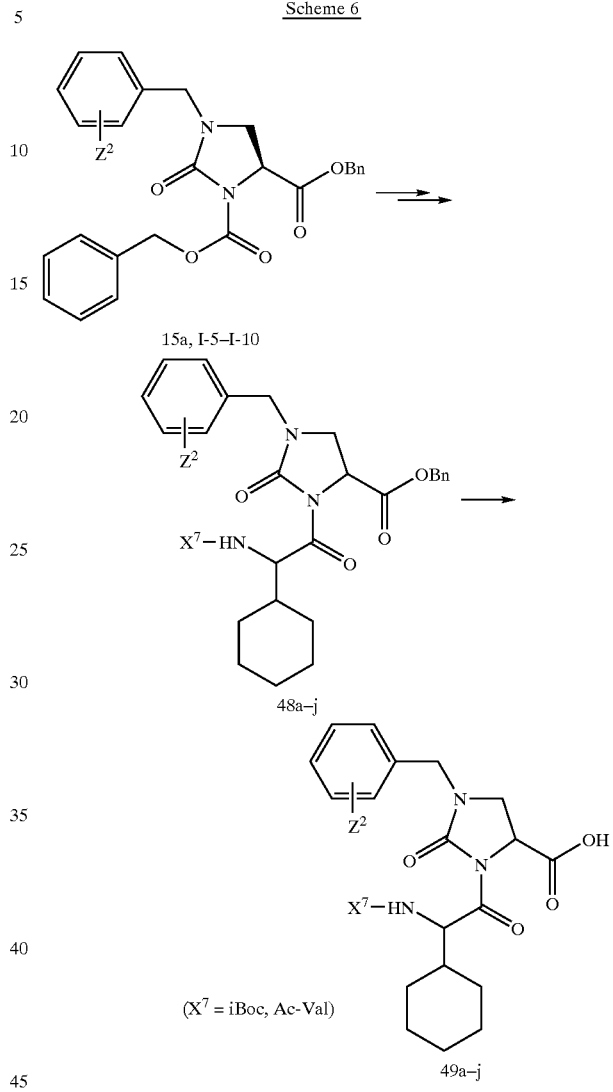

Synthesis of 49a–j: The precursors 48a–j were synthesized from appropriate building blocks (15a, I-5–I-10) using the procedures described earlier. Removal of the benzyl ester to provide the required compounds 49a–j were carried out using the procedure described for Example 3, Step E (reaction time=2–3 hrs) in quantitative yield.

Synthesis of 50a–i: Coupling reaction of 49a (0.12 mmol) with resin-bound compound H (0.039 mmol) was carried out as described for Intermediate H, Step 2 using HATU/DIPEA (0.12 mmol/0.24 mmol, reaction time=4 hrs) in DMF (2 mL). The reaction mixture was washed with DMF (4×4 mL), THF (2×4 mL) and dichloromethane (2×4 mL) to afford resin-bound compound 50a. Similar procedure was employed for the synthesis of 50b–j.

Synthesis of 51a–i: Resin-bound compound 50a (0.039 mmol) was treated with a solution of Dess-Martin's periodinane (0.16 mmol) and t-butanol (0.16 mmol) in dichloromethane (3 mL) at ambient temperature for 4 hrs. The resin was washed with 20% v/v iPrOH in dichloromethane (2×4 mL), THF (2×4 mL), 50% v/v aqueous THF (2×4 mL), THF (2×4 mL), and dichloromethane (4×4 mL) to provide resin-bound compound 51a. Similar procedure was employed for the synthesis of 51b–j.

Synthesis of 48–57: To the resin-bound compound 51a (0.039 mmol) was added 5% v/v TFA in dichloromethane (4 mL). After shaking for 5 minutes, the reaction mixture was filtered into a vial containing AcOH (1 mL). The filtrate was concentrated by vacuum centrifugation to afford the desired compound 48. Similar procedure was used for the synthesis of 49–57.

Scheme 7

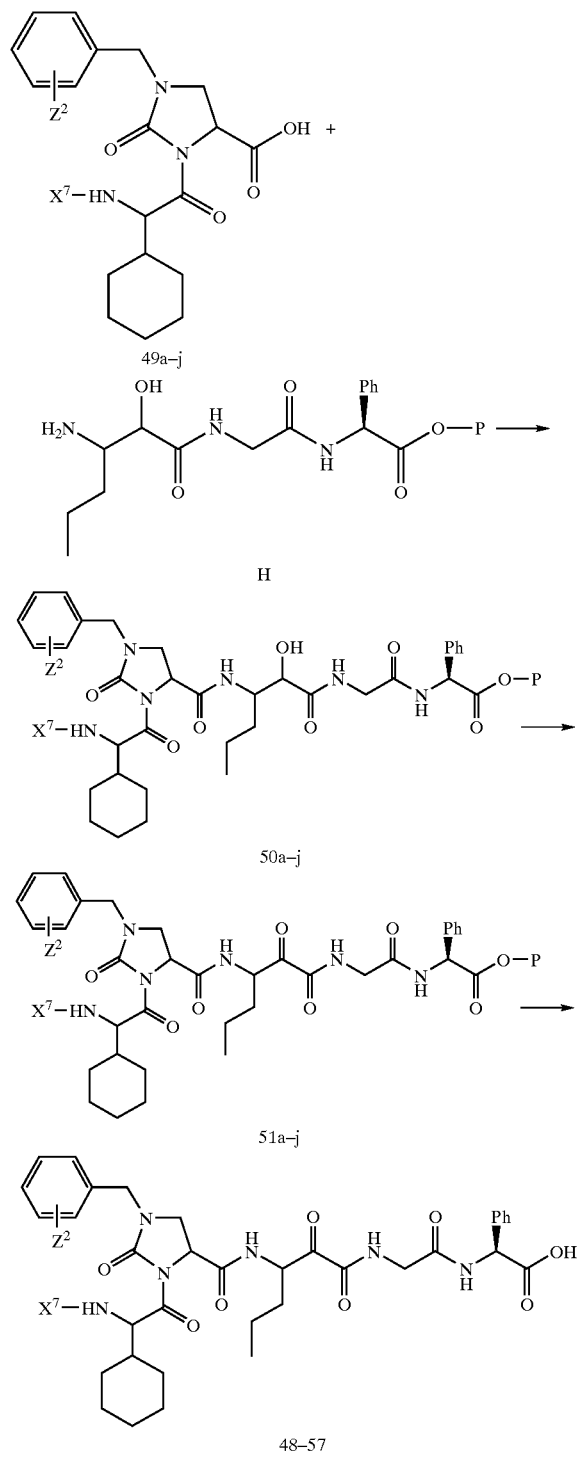

TABLE 9

| Compound | X[7] | Z[2] | M + H (LC-MS) |
|---|---|---|---|
| 48 | iBoc- | H | 777.2 |
| 49 | Ac-Val- | H | 818.2 |
| 50 | iBoc- | 3,4-dimethyl | 805.2 |
| 51 | Ac-Val- | 3,4-dimethyl | 846.2 |
| 52 | iBoc- | 3-methyl | 791.2 |
| 53 | Ac-Val- | 3-methyl | 832.2 |
| 54 | Ac-Val- | 4-methyl | 832.2 |
| 55 | Ac-Val- | 3-methoxy | 848.2 |
| 56 | Ac-Val- | 4-methoxy | 848.2 |
| 57 | Ac-Val- | 4-t-butyl | 874.2 |

Assay for HCV Protease Inhibitory Activity:

Spectrophotometric Assay: Spectrophotometric assay for the HCV serine protease was performed on the inventive compounds by following the procedure described by R. Zhang et al., *Analytical Biochemistry*, 270 (1999) 268–275, the disclosure of which is incorporated herein by reference. The assay based on the proteolysis of chromogenic ester substrates is suitable for the continuous monitoring of HCV NS3 protease activity. The substrates were derived from the P side of the NS5A—NS5B junction sequence (Ac-DTEDVVX(Nva) (SEQ ID NO: 1), where X=A or P) whose C-terminal carboxyl groups were esterified with one of four different chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation: Recombinant heterodimeric HCV NS3/NS4A protease (strain 1a) was prepared by using the procedures published previously (D. L. Sali et al, *Biochemistry*, 37 (1998) 3392–3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates was done as reported by R. Zhang et al, (ibid.) and was initiated by anchoring Fmoc-Nva-OH to 2-chlorotrityl chloride resin using a standard protocol (K. Barlos et al, int. J. Pept. Protein Res., 37 (1991), 513–520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, Acta Chem. Scand., B33 (1979) 410–412). Peptide fragments were dissolved in anhydrous pyridine (30–60 mg/ml) to which 10 molar equivalents of chromophore and a catalytic amount (0.1 eq.) of paratoluenesulfonic acid (pTSA) were added. Dicyclohexylcarbodiimide (DCC, 3 eq.) was added to initiate the coupling reactions. Product formation was monitored by HPLC and found to be complete following 12–72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20–30%. The molecular mass was confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD-substrate OD)/substrate OD).

Protease Assay: HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 150 µl mixtures of buffer, substrate and inhibitor were placed in wells (final concentration of DMSO 4% v/v) and allowed to preincubate at 30° C. for approximately 3 minutes. Fifty µls of pre-warmed protease (12 nM, 30° C.) in assay buffer, was then used to initiate the reaction (final volume 200 µl).The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6–200 µM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators: The inhibition constants ($K_i$) for the competitive inhibitors Ac-D-(D-Gla)-L-I-(Cha)-C-OH (27) (SEQ ID NO: 2), Ac-DTEDVVA(Nva)-OH (SEQ ID NO: 3) and Ac-DTEDVVP(Nva)-OH (SEQ ID NO: 4) were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i^*$ value.

The obtained $K_i^*$ values for the various compounds of the present invention are given in the afore-mentioned Table wherein the compounds have been arranged in the order of ranges of $K_i^*$ values. From these test results, it would be apparent to the skilled artisan that the compounds of the invention have excellent utility as NS3-serine protease inhibitors.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, including enantiomers, stereoisomers, rotamers and tautomers of said compound, and pharmaceutically acceptable salts or solvates of said compound, said compound having the general structure shown in Formula I:

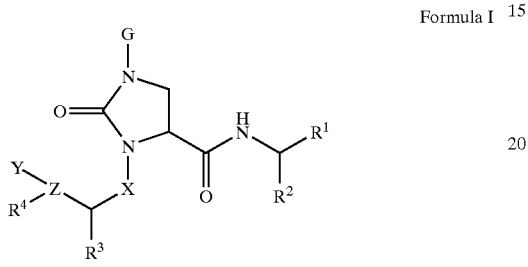

Formula I wherein:

R' is $COR^5$ or $B(OR)_2$, wherein $R^5$ is selected from the group consisting of: H, $CF_3$, $C_2F_5$, $C_3F_7$, $CF_2R^6$, $R^6$, and $OCR^7$ with $R^7$ being H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COO\ R^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COO\ R^{11}$, $CH(R^{1'})CONHCH(R^{2'})CONHCH(R^{3'})CONR^{12}R^{13}$, wherein $R^{1'}$, $R^{2'}$, $R^{3'}$, R', $R^{11'}$, $R^{12}$, and $R^{13}$ are independently selected from a group consisting of H, alkyl, aryl, heteroalkyl, heteroaryl, cycloalkyl, alkyl-aryl, alkyl-heteroaryl, aryl-alkyl and heteroaralkyl;

Z is O, N, or CH;

X is selected from the group consisting of: C=O, C=S and $(CRR')_p$;

p is a number from 1–6;

G is selected from the group consisting of: H, alkyl, aryl, heteroalkyl, heteroaryl, alkyl-aryl and alky-heteroaryl with the proviso that G may be additionally optionally and chemically-suitably substituted with $U^{11}$ or $U^{12}$;

$R^2$ is selected from the group consisting of H: C1–C10 alkyl: C2–C10 alkenyl; C3–C8 cycloalkyl: C3–C8 heterocycloalkyl, alkoxy, aryloxy, alkylthio, arylthio, amino, carbamate, urea, ketone, aldehyde, cyano, nitro; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

R, and $R^3$ may be the same or different and are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, ester, carboxylic acid, carbamate, urea, ketone, aldehyde, cyano, nitro; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

$R^4$ maybe present or absent, and if $R^4$ is present, $R^4$ is selected from H, alkyl, aryl; and Y is selected from the group consisting of H, alkyl, aryl, heteroalkyl, heteroaryl, cycloalkyl, arylalkyl, heteroarylalkyl, and U, where U is selected from alkyl-aryl, aryl-heteroaryl, alkyl-heteroaryl, alkylcarbonyl, arylalkylcarbonyl, arylcarbonyl, heteroalkylcarbonyl, heteroarylcarbonyl, cycloalkylcarbonyl, alkyloxycarbonyl, alkyl-aryloxycarbonyl, aryloxycarbonyl, arylalkyloxycarbonyl, heteroaryloxycarbonyl, heterocycloalkyloxycarbonyl, cycloalkyloxycarbonyl, alkylaminocarbonyl, arylaminocarbonyl, alkyl-arylaminocarbonyl, arylaminocarbonyl, arylalkylaminocarbonyl, heteroarylaminocarbonyl, cycloalkylaminocarbonyl, heterocycloalkylaminocarbonyl, alkylsulfonyl, arylsulfonyl, alkyl-arylsulfonyl, arylalkylsulfonyl, heteroarylsulfonyl, cycloalkylsulfonyl, and heterocycloalkylsulfonyl with the proviso that U may be additionally optionally and chemically-suitably substituted with $U^{11}$ or $U^{12}$; where $U^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl moiety, with the proviso that $U^{11}$ may be additionally optionally substituted with $U^{12}$; and $U^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from $U^{12}$; and that said moiety:

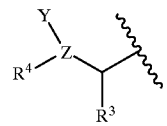

may alternately represent an arylalkyloxy group; with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, and hydroxamate.

2. The compound of claim 1, wherein $R^1$ is $OCR^5$, and $R^5$ is H, $COOR^8$, or $CONR^9R^{10}$.

3. The compound of claim 2, wherein $R^1$ is $COCONR^9R^{10}$, and is $R^9$ is H, and $R^{10}$ is H, $CH_2$—$CH=CH_2$, $CH(R^{1'})COOR^{11}$, $CH(R^{1'})$ $CONR^{12}R^{13}$, $CH(R^{1'})$ $CONHCH(R^{2'})COOR^{11}$, $CH(R^{1'})CONHCH(R^{2'})$ $CONR^{12}R^{13}$, or $CH(R^{1'})CONHCH(R^{2'})(R')$.

4. The compound of claim 3, wherein $R^{10}$ is $CH_2$—$CH=CH_2$.

5. The compound of claim 3, wherein $R^{10}$ is $CH(R^{1'})COOR^{11}$.

6. The compound of claim 5, wherein $R^{1'}$ is H and $R^{11}$ is H, allyl or benzyl.

7. The compound of claim 3, wherein $R^{10}$ is $CH(R^{1'})CONHCH(R^{2'})COOR^{11}$, $CH(R^{1'})CONHCH(R^{2'})CONR^{12}R^{13}$, or $CH(R^{1'})CONHCH(R^{2'})(R')$, wherein $R^{1'}$ is H and $R^{2'}$ is phenyl, substituted phenyl, heteroatom-substituted phenyl, thiophenyl, cyclohexyl, cyclopentyl, cyclopropyl, piperidyl or pyridyl.

8. The compound of claim 3, wherein $R^{10}$ is selected from the group consisting of $CH_2CONHCH(Ph)COOH$, $CH_2CONHCH(Ph)CONH_2$, $CH_2CONHCH(Ph)CONMe_2$ and $CH_2CONHCH(Ph)COO$-benzyl.

9. The compound of claim 1, wherein $R^2$ is selected from the group consisting of the following moieties:

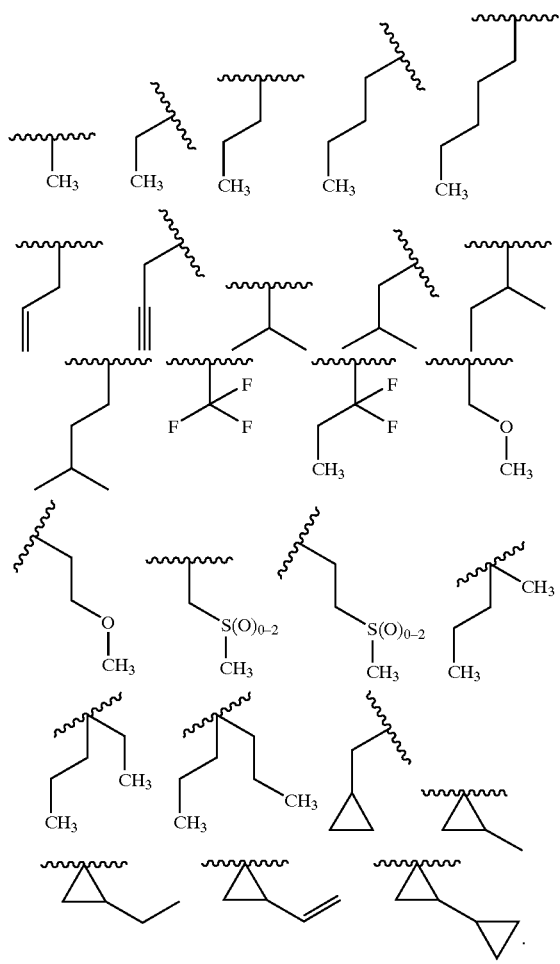

10. The compound of claim 1, wherein G is selected from the group consisting of:

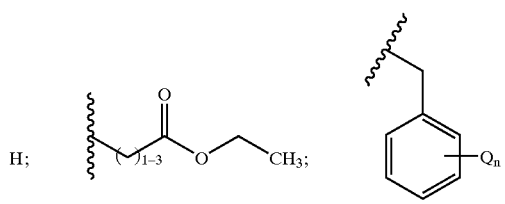

wherein n is a number from 0–2 and Q is selected from the group consisting of Cl, Br, methyl, methoxy, tert-butyl and combinations thereof.

11. The compound of claim 1, wherein X is C=O.

12. The compound of claim 1, wherein $R^3$ is selected from the group consisting of:

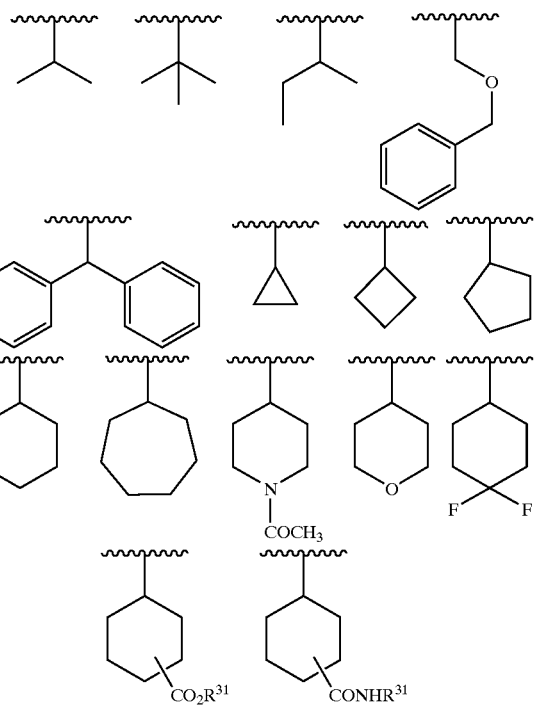

wherein $R^{31}$=H, alkyl or aryl.

13. The compound of claim 1, wherein said moiety:

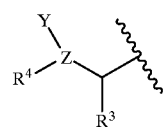

represents an arylalkyloxy group.

14. The compound of claim 13, wherein said arylalkyloxy group is benzyloxy.

15. The compound of claim 1, wherein Z is N and $R^4$ is H.

16. The compound of claim 1, wherein Y is selected from the group consisting of H, acetyl, or alkoxycarbonyl.

17. A compound, including enantiomers, stereoisomers, rotamers and tautomers of said compound, and pharmaceutically acceptable salts or solvates of said compound, said compound having the general structure shown in Formula II:

Formula II

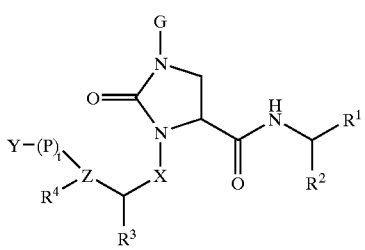

wherein:

t is a number from 1 to 3; and when t is 2 or 3, the P moieties may be the same or different;

P is represented by:

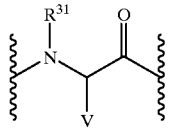

wherein V is selected from the group consisting of the following:

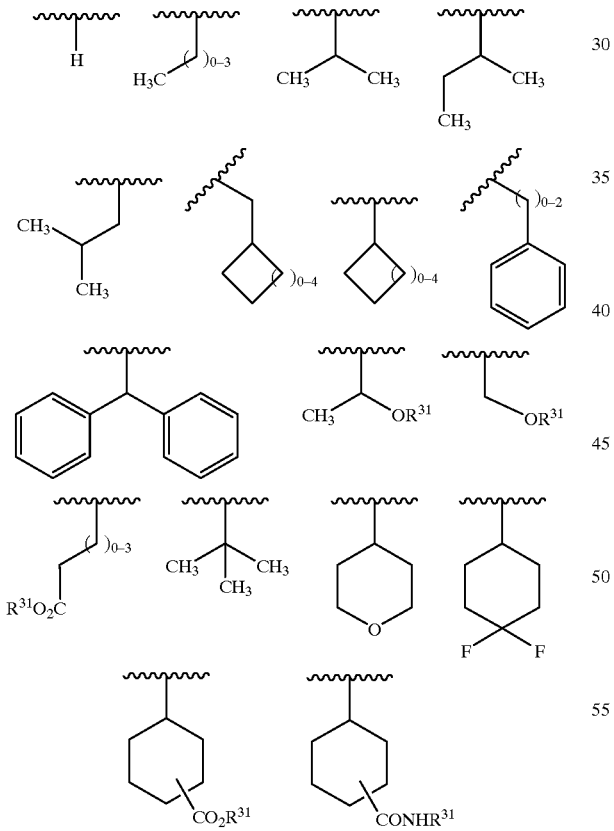

wherein $R^{31}$ is independently selected from H, alkyl or aryl;

$R^1$ is $COR^5$ or $B(OR)_2$, wherein $R^5$ is selected from the group consisting of: H, $CF_3$, $C_2F_5$, $C_3F_7$, $CF_2R^6$, $R^6$, and $COR^7$ with $R^7$ being H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{2'})CONR^{12}R^{13}$, $CH(R^{1'})CONHCH(R^{2'})COO$ $R^{11}$, $CH(R^{1'})CONHCH(R^{1'})CONR^{12}R^{13}$, $CH(R^{1'})CONHCH(R^{2'})R'$, $CH(R^{1'})CONHCH(R^{2'})CONHCH(R^{3'})COO$ $R^{11}$, $CH(R^{1'})CONHCH(R^{2'})CONHCH(R^{3'})CONR^{12}R^{13}$, wherein $R^{1'}$, $R^{2'}$, $R^{3'}$, $R'$, $R^{11}$, $R^{12}$, and $R^{13}$ are independently selected from a group consisting of H, alkyl, aryl, heteroalkyl, heteroaryl, cycloalkyl, alkyl-aryl, alkyl-heteroaryl, aryl-alkyl and heteroaralkyl;

Z is O, N, or CH;

X is selected from the group consisting of: C=O, O=S and $(CRR')_p$;

p is a number from 1–6;

G is selected from the group consisting of: H, alkyl, aryl, heteroalkyl, heteroaryl, alkyl-aryl and alky-heteroaryl with the proviso that G may be additionally optionally and chemically-suitably substituted with $U^{11}$ or $U^{12}$;

$R^2$ is selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, carbamate, urea, ketone, aldehyde, cyano, nitro; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

R, and $R^3$ may be the same or different and are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, ester, carboxylic acid, carbamate, urea, ketone, aldehyde, cyano, nitro; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

$R^4$ maybe present or absent, and if $R^4$ is present, $R^4$ is selected from H, alkyl, aryl; and Y is selected from the group consisting of H, alkyl, aryl, heteroalkyl, heteroaryl, cycloalkyl, arylalkyl, heteroarylalkyl, and U, where U is selected from alkyl-aryl, aryl-heteroaryl, alkyl-heteroaryl, alkylcarbonyl, arylalkylcarbonyl, arylcarbonyl, heteroalkylcarbonyl, heteroarylcarbonyl, cycloalkylcarbonyl, alkyloxycarbonyl, alkyl-aryloxycarbonyl, aryloxycarbonyl, arylalkyloxycarbonyl, heteroaryloxycarbonyl, heterocycloalkyloxycarbonyl, cycloalkyloxycarbonyl, alkylaminocarbonyl, arylaminocarbonyl, alkyl-arylaminocarbonyl, arylaminocarbonyl, arylalkylaminocarbonyl, heteroarylaminocarbonyl, cycloalkylaminocarbonyl, heterocycloalkylaminocarbonyl, alkylsulfonyl, arylsulfonyl, alkyl-arylsulfonyl, arylalkylsulfonyl, heteroarylsulfonyl, cycloalkylsulfonyl, and heterocycloalkylsulfonyl with the proviso that U may be additionally optionally and chemically-suitably substituted with $U^{11}$ or $U^{12}$; where $U^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl moiety, with the proviso that $U^{11}$ may be additionally optionally substituted with $U^{12}$; and U$^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from U$^{12}$; with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, and hydroxamate.

18. The compound of claim 17, wherein R$^1$ is OCR$^5$, and R$^5$ is H, GN, COOR$^8$, or CONR$^9$R$^{10}$.

19. The compound of claim 18, wherein R$^1$ is COCONR$^9$R$^{10}$, and is R$^9$ is H, and R$^{10}$ is H, CH$_2$—CH=CH$_2$, CH(R$^{1'}$)COOR$^{11}$, CH(R$^{1'}$) CONR$^{12}$R$^{13}$, CH(R$^{1'}$)CONHCH(R$^{2'}$)COOR$^{11}$, CH(R$^{1'}$)CONHCH(R$^{2'}$) CONR$^{12}$R$^{13}$, or CH(R$^{1'}$)CONHCH(R$^{2'}$)(R').

20. The compound of claim 19, wherein R$^{10}$ is CH$_2$—CH=CH$_2$.

21. The compound of claim 19, wherein R$^{10}$ is CH(R$^{1'}$)COOR$^{11}$.

22. The compound of claim 21, wherein R$^{1'}$ is H and R$^{11}$ is H, allyl or benzyl.

23. The compound of claim 19, wherein R$^{10}$ is CH(R$^{1'}$)CONHCH(R$^{2'}$)COOR$^{11}$, CH(R$^{1'}$)CONHCH(R$^{2'}$)CONR$^{12}$R$^{13}$, or CH(R$^{1'}$)CONHCH(R$^{2'}$)(R'), wherein R$^{1'}$ is H and R$^{2'}$ is phenyl, substituted phenyl, heteroatom-substituted phenyl, thiophenyl, cyclohexyl, cyclopentyl, cyclopropyl, piperidyl and pyridyl.

24. The compound of claim 19, wherein R$^{10}$ is selected from the group consisting of CH$_2$CONHCH(Ph)COOH, CH$_2$CONHCH(Ph)CONH$_2$, CH$_2$CONHCH(Ph)CONMe$_2$ and CH$_2$CONHCH(Ph)CO—O-benzyl.

25. The compound of claim 17, wherein R$^2$ is selected from the group consisting of the following moieties:

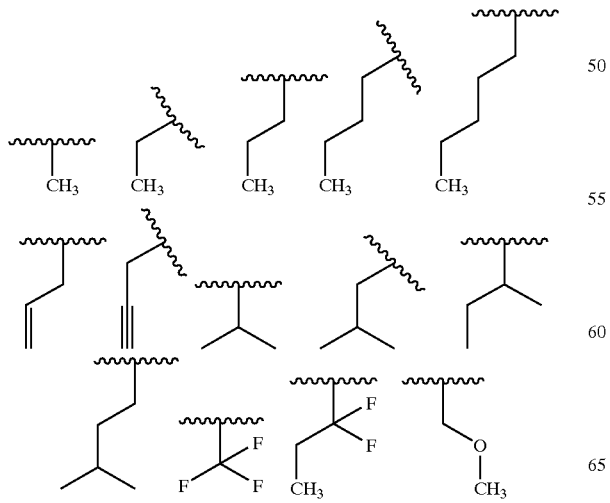

-continued

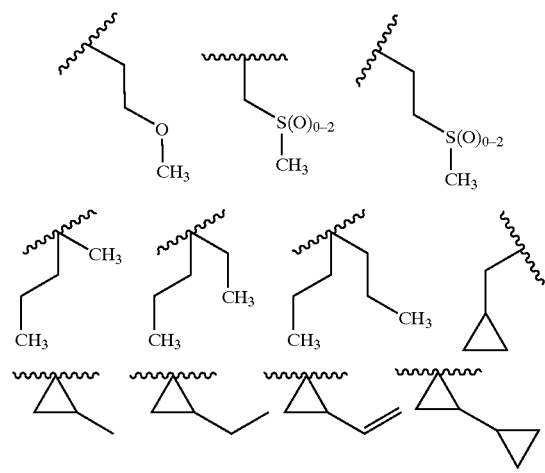

26. The compound of claim 17, wherein G is selected from the group consisting of:

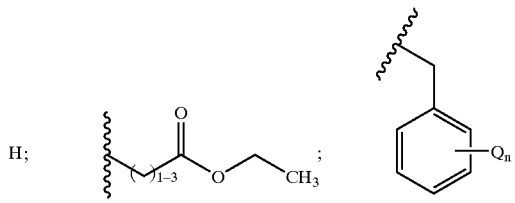

wherein n is a number from 0–2 and Q is selected from the group consisting of Cl, Br, methyl, methoxy, tert-butyl and combinations thereof.

27. The compound of claim 17, wherein X is C=O.

28. The compound of claim 17, wherein R$^3$ is selected from the group consisting of:

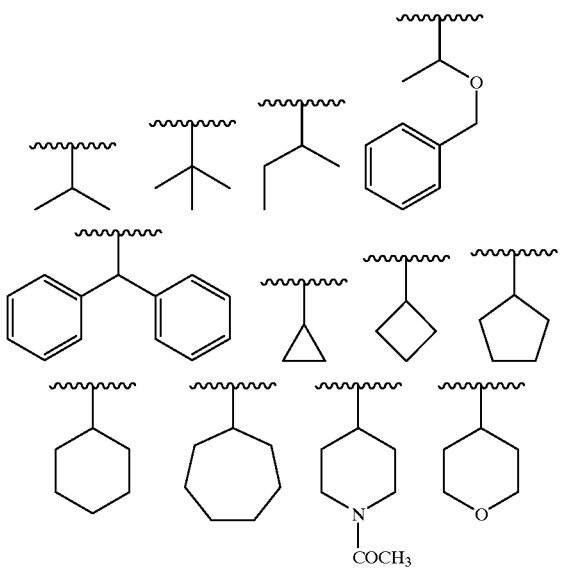

-continued

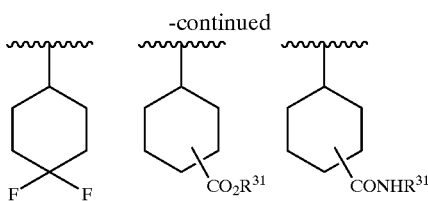

wherein R³¹=H, alkyl or aryl.

29. The compound of claim 17, wherein Z is N and R⁴ is H.

30. The compound of claim 17, wherein P is a peptide moiety selected from Glu(O′Bu)-Glu(O′Bu)-Val and Glu-Glu-Val.

31. The compound of claim 17, wherein P is an amino acid moiety selected from Val, Glu(O′Bu) and Glu.

32. The compound of claim 17, wherein t is 1.

33. The compound of claim 17, wherein t is 3.

34. The compound of claim 17, wherein Y is selected from the group consisting of H, acyl, or alkoxycarbonyl.

35. The compound of claim 34, wherein the acyl group is acetyl group.

36. A composition comprising as an active ingredient a compound of claim 1 or claim 17 and a pharmaceutically acceptable carrier.

37. The composition of claim 36 wherein said compound is present in an amount effective to inhibit hepatitis C nonstructural protein-3 protease (HCV NS3 protease).

38. A method preparing a composition comprising bringing into intimate contact a pharmaceutically acceptable carrier and a compound of claim 1 or claim 17 in an amount effective to inhibit hepatitis C nonstructural protein-3 protease (HCV NS3 protease).

39. A compound exhibiting HCV protease inhibitory activity, including enantiomers, stereoisomers and tautomers of said compound, and pharmaceutically acceptable salts or solvates of said compound, said compound being selected from the compounds of structures listed below:

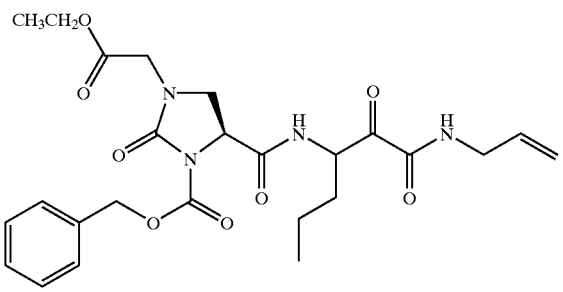

1

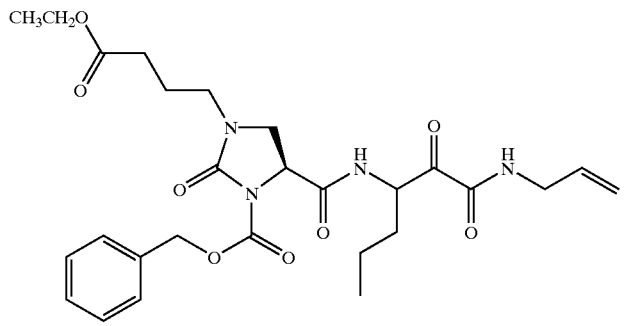

2

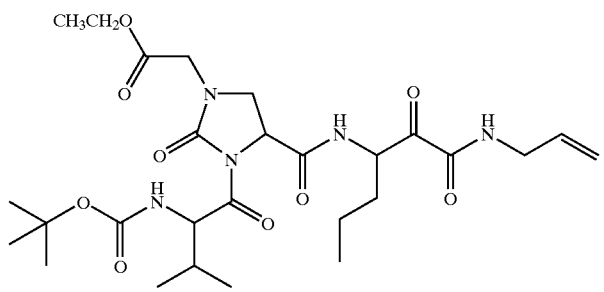

3

-continued
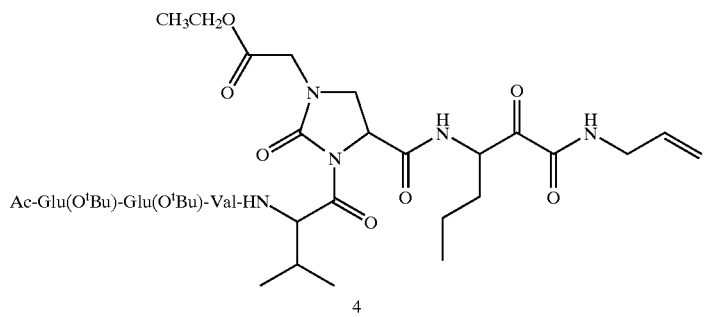
4
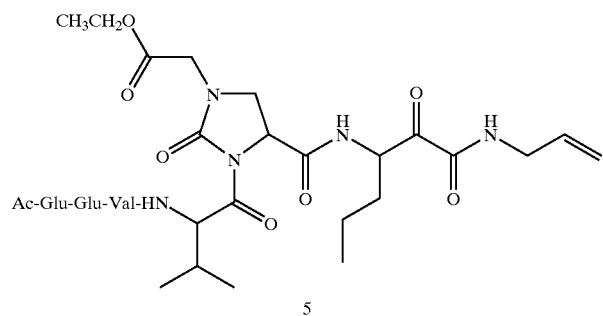
5
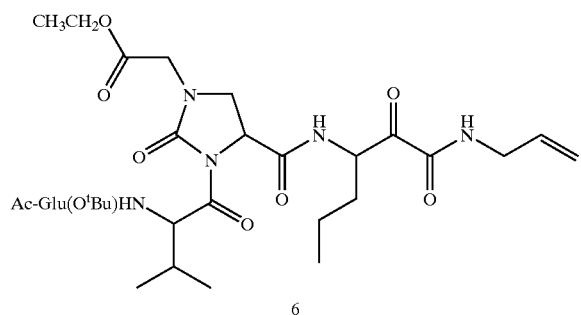
6
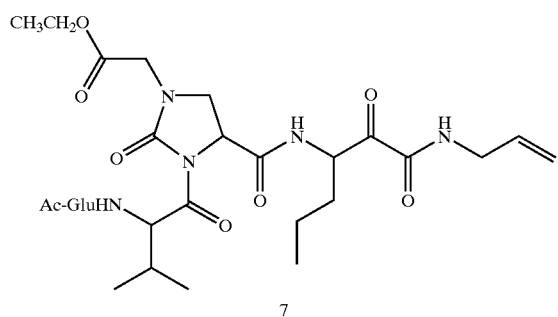
7
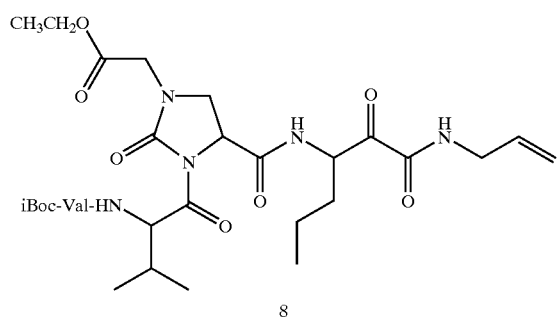
8

-continued
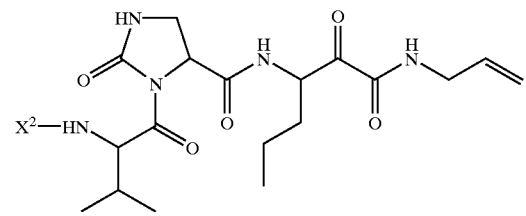
| Compound | X² |
|---|---|
| 9 | Boc-Val- (isomer 1) |
| 10 | Boc-Val- (isomer 2) |
| 11 | Ac-Glu(OᵗBu)-Glu(OᵗBu)-Val- |
| 12 | Ac-Glu-Glu-Val- |
| 13 | Boc |
| 14 | H |
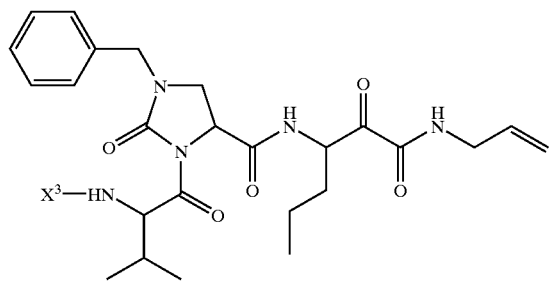
| Compound | X³ |
|---|---|
| 15 | Boc-Val- |
| 16 | Val- |
| 17 | Ac-Glu(OᵗBu)-Glu(OᵗBu)-Val- |
| 18 | Ac-Glu-Glu-Val- |
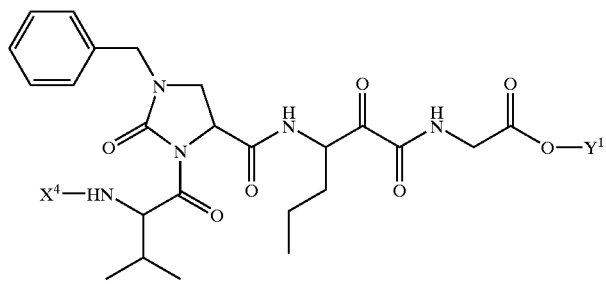
| Compound | X⁴ | Y¹ |
|---|---|---|
| 19 | Boc- | allyl |
| 20 | H | allyl |
| 21 | Boc-Val- | allyl |
| 22 | Ac-Glu(OᵗBu)-Glu(OᵗBu)-Val- | allyl |
| 23 | Ac-Glu-Glu-Val- | allyl |
| 24 | Boc-Val- | H |
| 25 | Ac-Glu(OᵗBu)-Glu(OᵗBu)-Val- | H |
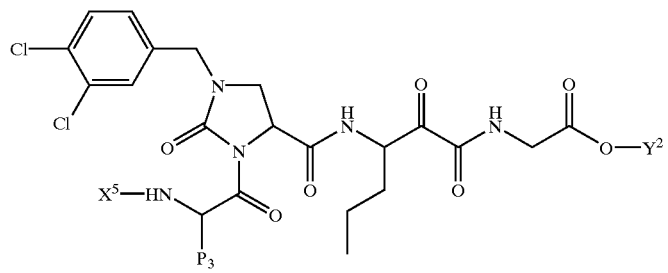

-continued

| Compound | $X^5$ | $Y^2$ | $P_3$ |
|---|---|---|---|
| 26 | Boc-Val- | allyl | iPr |
| 27 | Ac-Glu(O$^t$Bu)-Glu(O$^t$Bu)-Val- | allyl | iPr |
| 28 | Ac-Glu-Glu-Val- | allyl | iPr |
| 29 | Boc- | benzyl | Chx |

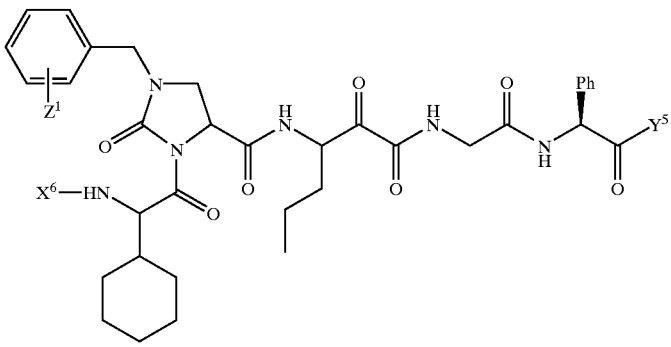

| Compound | $X^6$ | $Z^1$ | $Y^5$ |
|---|---|---|---|
| 30 | Boc- | 3,4-dichloro | —NH$_2$ |
| 31 | Boc- | 4-Bromo | —OBn |
| 32 | Boc- | 3-Bromo | —OBn |
| 33 | Boc- | 4-Chloro | —OBn |
| 34 | Boc- | 3-Chloro | —OBn |
| 35 | iBoc- | 3,4-dichloro | —NH$_2$ |
| 36 | iBoc- | 4-Bromo | —OBn |
| 37 | iBoc- | 3-Bromo | —OBn |
| 38 | iBoc- | 4-Chloro | —OBn |
| 39 | iBoc- | 3-Chloro | —OBn |
| 40 | Boc- | 4-Bromo | —OH |
| 41 | Boc- | 3-Bromo | —OH |
| 42 | Boc- | 4-Chloro | —OH |
| 43 | Boc- | 3-Chloro | —OH |
| 44 | iBoc- | 4-Bromo | —OH |
| 45 | iBoc- | 3-Bromo | —OH |
| 46 | iBoc- | 4-Chloro | —OH |
| 47 | iBoc- | 3-Chloro | —OH |

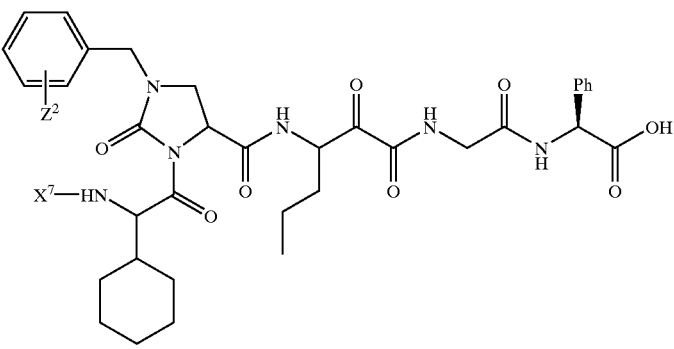

| Compound | $X^7$ | $Z^2$ |
|---|---|---|
| 48 | iBoc- | H |
| 49 | Ac-Val- | H |
| 50 | iBoc- | 3,4-dimethyl |
| 51 | Ac-Val- | 3,4-dimethyl |
| 52 | iBoc- | 3-methyl |
| 53 | Ac-Val- | 3-methyl |
| 54 | Ac-Val- | 4-methyl |
| 55 | Ac-Val- | 3-methoxy |
| 56 | Ac-Val- | 4-methoxy |
| 57 | Ac-Val- | 4-$^t$-butyl. |

40. A composition comprising a pharmaceutically acceptable carrier and one or more compounds of claim 39 in amount effective to inhibit hepatitis C nonstructural protein-3 protease (HCV NS3 protease.).

41. The composition of claim 40, additionally containing an antiviral agent.

42. The composition of claim 40 or claim 41, still additionally containing an interferon.

43. The composition of claim 42, wherein said antiviral agent is ribavirin and said interferon is α-interferon.

* * * * *

UNITED STATES PATENT AND TRADEMARK OFFICE
CERTIFICATE OF CORRECTION

PATENT NO. : 6,838,475 B2
DATED : January 4, 2005
INVENTOR(S) : Ashok Arasappan et al.

It is certified that error appears in the above-identified patent and that said Letters Patent is hereby corrected as shown below:

Column 67,
Line 29, please correct "$OCR^7$" to -- $COR^7$ --.

Column 69,
Line 1, please correct "$OCR^5$" to -- $COR^5$ --.
Line 4, please delete "is".

Column 72,
Line 3, please correct "$CH(R^2)$" to -- $CH(R^{1'})$ --.
Line 5, please correct "$CH(R^{1'})CONR^{12}R^{13}$" to -- $CH(R^{2'})CONR^{12}R^{13}$ --.
Line 14, please correct "O=S" to -- C=S --.

Column 73,
Line 22, please correct "$OCR^5$" to -- $COR^5$ --.

Signed and Sealed this

Fifth Day of April, 2005

JON W. DUDAS
*Director of the United States Patent and Trademark Office*